US012421186B2

(12) United States Patent
Camacho et al.

(10) Patent No.: US 12,421,186 B2
(45) Date of Patent: Sep. 23, 2025

(54) ORGANIC AMMONIUM SALTS WITH TRACEABILITY AND DETERGENT DISPERSANT PROPERTIES TO LIQUID FUELS AND PROCESSES FOR THEIR SYNTHESIS

(71) Applicant: Instituto Mexicano del Petróleo, Mexico City (MX)

(72) Inventors: Ricardo Cerón Camacho, Mexico City (MX); Raúl Oviedo Roa, Mexico City (MX); Jorge Francisco Ramírez Pérez, Mexico City (MX); Enrique Soto Castruita, Mexico City (MX); Rodolfo Cisneros Dévora, Mexico City (MX); David Aaron Nieto Álvarez, Mexico City (MX); José Manuel Martinez Magadan, Mexico City (MX); Ana Graciela Servín Nájera, Mexico City (MX); Luis Silvestre Zamudio Rivera, Mexico City (MX)

(73) Assignee: Instituto Mexicano del Petróleo, Mexico City (MX)

( * ) Notice: Subject to any disclaimer, the term of this patent is extended or adjusted under 35 U.S.C. 154(b) by 4 days.

(21) Appl. No.: 18/205,604

(22) Filed: Jun. 5, 2023

(65) Prior Publication Data
US 2024/0190812 A1    Jun. 13, 2024

(30) Foreign Application Priority Data
Nov. 29, 2022   (MX) .................. MX/a/2022/015075

(51) Int. Cl.
*C07C 245/08* (2006.01)
*C07C 211/63* (2006.01)
(Continued)

(52) U.S. Cl.
CPC .......... *C07C 245/08* (2013.01); *C07C 211/63* (2013.01); *C07C 215/40* (2013.01);
(Continued)

(58) Field of Classification Search
CPC ... C07C 211/07; C07C 211/21; C07C 211/63; C07C 215/08; C07C 215/40;
(Continued)

(56) References Cited

U.S. PATENT DOCUMENTS

2015/0034036 A1*  2/2015  Burgess ................ C10L 1/2387
                                                  44/422
2019/0367828 A1* 12/2019  Hansch ................. C10L 1/2225

* cited by examiner

Primary Examiner — Latosha Hines
(74) Attorney, Agent, or Firm — FisherBroyles, LLP; Jason P. Mueller

(57) ABSTRACT

The present invention is related to a process for obtaining organic ammonium salts (OAS) and their derivatives, supramolecular surfactants (SS), which simultaneously present the properties of traceability and detergents dispersant of organic scales. Organic ammonium salts (OAS) and their derivatives supramolecular surfactants (SS) have applications as differentiators, markers, or tracers in fuels derived from hydrocarbons; and also to disperse organic scales or inhibit the gums precipitation both in injectors and intake valves of automotive vehicle engines. Organic ammonium salts (OAS) are obtained through an acid-base reaction between a molecule from the azo family and an amine. Once the OAS is obtained, it reacts with an organic compound (OC) so that through non-covalent interactions, a self-assembly process occurs that gives rise to the SS. Said process is based on green chemistry, that is, in the absence of solvents. These OAS and SS are quantified through the analytical techniques of ultraviolet-visible (UV-VIS) and high-performance liquid chromatography (HPLC) through a
(Continued)

calibration curve. Additionally, its performance as a gum-dispersing agent in a single-cylinder engine is evaluated.

10 Claims, 9 Drawing Sheets

(51) Int. Cl.

| | | |
|---|---|---|
| C07C 215/40 | (2006.01) | |
| C07D 207/40 | (2006.01) | |
| C09B 29/01 | (2006.01) | |
| C09B 67/18 | (2006.01) | |
| C10L 1/222 | (2006.01) | |
| C10L 1/226 | (2006.01) | |
| C10L 1/232 | (2006.01) | |
| C10L 1/233 | (2006.01) | |
| C10L 10/06 | (2006.01) | |
| G01N 30/02 | (2006.01) | |
| G01N 30/74 | (2006.01) | |
| G01N 30/86 | (2006.01) | |
| G01N 33/28 | (2006.01) | |

(52) U.S. Cl.
CPC ........ *C07D 207/40* (2013.01); *C09B 29/0007* (2013.01); *C09B 67/002* (2013.01); *C10L 1/2222* (2013.01); *C10L 1/226* (2013.01); *C10L 1/232* (2013.01); *C10L 1/2335* (2013.01); *C10L 10/06* (2013.01); *G01N 30/74* (2013.01); *G01N 30/8624* (2013.01); *G01N 33/2835* (2013.01); *C10L 2200/0423* (2013.01); *C10L 2270/023* (2013.01); *G01N 2030/027* (2013.01)

(58) Field of Classification Search
CPC . C07C 245/08; C07D 207/40; C09B 29/0007; C09B 67/002; C09B 69/045; C10L 1/2222; C10L 1/226; C10L 1/232; C10L 1/2335; C10L 10/04; C10L 10/06; C10L 2200/0423; C10L 2230/16; C10L 2270/023; C10L 2270/026; G01N 2030/027; G01N 30/74; G01N 30/8624; G01N 30/8665; G01N 30/88; G01N 33/2835
See application file for complete search history.

ORGANIC AMMONIUM SALTS WITH TRACEABILITY AND DETERGENT DISPERSANT PROPERTIES TO LIQUID FUELS AND PROCESSES FOR THEIR SYNTHESIS

CROSS REFERENCE TO RELATED APPLICATIONS

This application claims priority under 35 USC 119 of Mexican patent application no. MX/a/2022/015075, filed in the Mexican Patent Office on Nov. 29, 2022.

TECHNICAL FIELD OF THE INVENTION

The present invention is related to a process for obtaining organic ammonium salts (OAS) and their corresponding supramolecular surfactants (SS), which have traceability and detergent dispersant properties against organic scales, and have applications in liquid fuels. The organic ammonium salts and their derivative supramolecular surfactants can be used to differentiate or mark gasoline or fuels derived from hydrocarbons and disperse organic scales or inhibit the precipitation of gums in injection and intake valves of motor vehicle engines. The process for their synthesis is according to green chemistry, and the quantification is carried out through analytic techniques of ultraviolet-visible (UV-VIS) and high-performance liquid chromatography (HPLC).

BACKGROUND OF THE INVENTION

Worldwide there exists a serious problem of fuel theft, that leads to many other problems, such as modification of the original stolen fuel formulation (adulteration) and smuggling or illegally selling these fuels. As a consequence, fuel marking is an activity that has been developed in the last two decades. Creating solutions that involve using chemicals with traceability, marking, differentiates, or dyes properties, which are detected through some analytic techniques, such as ultraviolet-visible spectrometry (UV-VIS), infrared spectroscopy (FT-IR), fluorescence, and adsorption chromatography in a column by gravity and gas chromatography coupled to different detectors like mass spectrometry or fluorescence, also, although less by high-performance liquid chromatography (HPLC).

Besides preventing theft, adulteration, and gasoline smuggling, the markers are a differentiator between competitors or operators that deliver and distribute fuels, which allows differentiation of the product offered in the fuel market. Therefore, the determination and quantification of these markers are critical.

Among the chemicals widely used as markers are those that have the property of being dyes. Particularly, and according to European patent EP1580254A2, a marker is a compound or composition that marks hydrocarbon-based fuels, is resistant to removal from fuels, is resistant to alteration, is resistant to destruction or decomposition, and is resistant to masking its effect. In addition, it provides a unique characteristic to the fuel so that it can be identified and differentiated from other hydrocarbon-based fuels.

Dyes from the azo (1) chemical family are the most widely used due to their low cost and because they can easily be incorporated into hydrocarbon-based fuels.

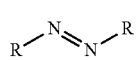
(1)

The chemical family azo is characterized by a double bond N=N. Their substituents R groups could be the same or different (R=aromatic, linear, or branched alkyl chain, with polar or electro-attractor substituents). These markers for fuels can contain only one azo molecule or be a composition from at least two or more azo derivatives.

So is described the inventions and scientific articles related to using chemicals with traceability or markers or dye properties in liquid fuels and their corresponding determination.

The European patent application EP1580254A2 discusses detecting markers from the chemical family azo in fuels by measuring its absorbance using the UV-VIS technique. This document does not protect the detection limits or umbral of concentrations employed in the fuels.

In the England patent application GB2535179A, is mentioned the formulation and marking method for hydrocarbon-based fuels, lubricants, and oils, wherein the chemical family azo is employed as dyes. The formulation highlights the use of aromatic naphtha to dilute previously the marker that can be used in kerosene, lubricants, gasoline, diesel, and jet fuels. The maker's quantification ranges from 1 to 100 ppm; however, the quantification method employed is a gravimetric type through ASTM D2276.

The U.S. Pat. No. 5,156,653A refers silent markers to liquid petroleum products. It describes that employment of phenyl-azo phenols derivatives to mark liquid petroleum products. The invention mentions an extraction method that uses a mixture of water, diethylene glycol, and methoxy-ethoxy propylamine to separate the marker from fuels such as diesel. Whereas, when the marker is extracted, it is spectrometry measured at 592 nm, and the absorbance is compared with the corresponding calibration curve to detect the marker, where it showed a concentration value concerning the original marking. However, it has the disadvantage of doing the extraction and not permitting direct detection from the fuel without previous treatment.

It is known that the compounds solvent orange 7 and solvent red 24 were studied as markers in gasoline samples. These studies employ the HPLC technique coupled with UV-Vis detection. These dyes are separated in reverse phase C-18 column with a mobile phase of acetonitrile/water. Which entails a pretreatment protocol of the fuel sample, consisting of the sample evaporation, reconstitution, and previous pretreatment over a silica cartridge. This sample is analyzed through HPLC and detected by UV-VIS at 490 or 640 nm. It is built on a conventional calibration curve, and it is determined the marker amount in the range of 0.5-30 ppm. As well as the detection limits are between 0.05 and 0.85 ppm; however, this study discusses the fuel matrix does not permit direct sample use to analyze, whereby to eliminate this effect, they must be done the pretreatment. (M. A. Gonçalves Trindade, M. V. Boldrin Zanoni, F.-M. Matsik. Fuel, 89, 2010, 2463-2467).

Another known reference to mention is the study on markers of the azo type, such as solvent red 19 and yellow 124, that, besides employing HPLC in its quantification, is the following: in real fuel samples, the method allows fuel marking and after a filtration process, the fuel sample to analyze is injected to an HPLC chromatogram, equipped with a Zorbax Rx-SIL column, and employ a mobile phase of hexane, toluene, and ethyl acetate; with UV-VIS detection at 390 and 535 nm. The range studied is between 1-10 ppm, employing a calibration curve with which real diesel samples have been analyzed. It found that the method is adequate to determine the markers. However, it is mentioned that the markers are not pure or are isomer mixture or other markers since they do not match the results found with the official concentration dosed (A. Markevicius, A. Zolumskis, A. Sadaunykas, et al. CHRMIJA, 2018, 29, 121-126).

Another research paper also exposes that have been done studies about dyes characterization through liquid chromatographic techniques coupled with mass spectrometry (HPLC-MS). This article is characterized by azo, diazo, and anthraquinone dyes on gasoline. The column used is a Zorbax C18 type. And respect to the sample preparation consists of the dose of the gasoline with 1 ppm of the azo compound to simulate a typical concentration in commercial gasoline. Then, the marked gasoline is passed through a silica gel Sep-PAK column to separate polar hydrocarbons. Once the sample is conditioned, it is evaporated with nitrogen and reconstituted in methanol to be injected into the HPLC-MS system. The method is capable of detecting until 10 ppt (parts per trillion) and 100 ppb (parts per billion). Although it is mentioned that it is adequate to typical intervals between 2-0.5 ppm of the marker, and also discussed that the polar components in gasoline darken the chromatograms with UV detection but not produces interference in HPLC-MS, even though it is necessary, the preconditioning of the sample. (R. D. Voyksner, Anal. Chem. 1985, 57, 2600-2605).

Another marked fuel samples study discusses a liquid chromatographic method to analyze the dye solvent yellow 124 in fuel diesel samples. This method can detect an azo derivative in diesel samples. However, the samples are diluted with hexane and previously filtered through a silica gel-packed column to separate the part containing the marker; then, the sample is injected in an HPLC with a YMC C8-AQ column and diodes detector. The system's linearity is between 0.5-100 nm of dye, with a detection limit of 60-80 pg. The disadvantage of the method is the sample preparation before the injection; besides, it is not directly quantifiable but detects the presence/absence of the marker (S. Henricsson, R. Westerholm, J. Chomat. A, 1996, 723, 395-398).

The U.S. Pat. No. 5,504,199A mentions that it can introduce dyes such as phenyl azo types or phenyl alkyl azo derivatives and 1,4-dialkyl anthraquinones, which are generally insoluble in ethanol. This is done using the dye in addition to a nonionic surfactant to compatibilist the mixture with ethanol and a solvent to produce a homogeneous solution. The invention describes oil fuel dyes or markers for visual identification with dyes designed as "solvent dyes" wherein an alternative to the oil fuels is ethanol, which also must be used in internal combustion engines. These dyes typically are added between 1-100 ppm. However, they are very insoluble in ethanol, whereby the method consists of introducing a "solvent dye" in ethanol through a mixture with red marker B dissolved in xylene (65% weight of marker, 35% weight of xylene); with nonyl phenol ethoxylated as a nonionic surfactant in weight percentage ratio of the dye 50-85% with 32.5-55-3% of nonionic surfactant. The document does not reveal more details about the composition or any quantification method.

It is known that compounds of quaternary ammonium salts or organic ammonium salts type exist that, according to the substituent (or along the alkyl chain) to nitrogen, can show surfactant properties. That may have applications in liquids hydrocarbons (A. Dolan, R. Atkin, G. Warr. Chem. Sci. 2015, 6, 6189). The following inventions and research papers are related to this topic.

The European patent EP2578667B1 relates to using a quaternary ammonium salt additive in a gasoline composition to improve the performance of a gasoline engine with direct injection and spark ignition. The additive is composed of one or more quaternary ammonium salts formed by the reaction of the ester of a carboxylic acid, selected from among an aromatic carboxylic acid, an $\alpha$-hydroxycarboxylic acid, and a polycarboxylic acid with a tertiary amine.

The European patent EP3581638B1 relates to gasoline additive compositions which include quaternary ammonium salts soluble in hydrocarbon solvents, and to methods of using the salts in a fuel composition as detergents for fuels. The quaternary ammonium salts are formed by the reaction of an alkyl carboxylate with an amido or imide compound obtained by the reaction of an acylating agent, substituted with a hydrocarbyl and an amine.

The existence of a theoretical-experimental study on the molecular interactions between ionic liquids and asphaltenes is also pointed out, where it was found that the ionic liquids derived from tetradecyl-trimethylammonium (quaternary ammonium salts) alter the association of asphaltene dimers through the supramolecular complexes formation that modifies the properties of the heavy crude oil, such as viscosity and interfacial tension. In this study, a solution to disperse organic type scale is discussed (R. Hernández-Bravo, A. D. Miranda, J. M. Martínez-Magadán, J. M. Domínguez. J. Phys. Chem. B. 2018, 122, 4325-4335).

The U.S. Pat. No. 4,248,719 describes quaternary ammonium salts prepared by a reaction of an alkenyl succinimide with a monocarboxylic acid ester. Which provides improved dispersion in lubricating oils compared to the initial alkenyl succinimides.

The U.S. Pat. No. 8,147,569B2 describes a quaternary ammonium salt detergent obtained by reaction of (a) an acylating agent substituted with hydrocarbyl and a compound containing an oxygen or nitrogen atom capable of condensing with said acylating agent and further containing a tertiary amino group; and (b) a suitable agent to convert the tertiary amino group to a quaternary nitrogen. Also, it describes using such detergents composed of quaternary ammonium salts in a fuel composition to reduce intake valve deposits.

The U.S. Pat. No. 8,915,977B2 describes a soluble gasoline additive for a gasoline engine, which includes a quaternary ammonium salt derived from an amidoamine containing at least one tertiary amino group and an epoxide, with the presence of a proton donor selected from a carboxylic acid and an alkyl phenol. The amidoamine is obtained from a reactive medium substantially devoid of an acylating agent.

The U.S. Pat. No. 9,506,006B2 provides a composition and a concentrate comprising (a) a greater amount of oil with lubricating viscosity, (b) a quaternary ammonium salt product of the condensation of an acylating agent substituted with hydrocarbyl, and (c) an optional amount of succinimide dispersant, different than (b). Also, the invention provides the use of a quaternary ammonium salt, which is the condensation product of an acylating agent, substituted with hydrocarbyl as a synergistic dispersant combination with a succinimide dispersant.

The U.S. Pat. No. 9,677,020B2 presents fuel additive compositions, as well as fuels that include the additive composition, which helps improve the performance of fuel injection engines, reducing engine wear and improving the demulsibility of fuels. The fuel additive compositions include quaternary ammonium carboxylates, soluble in hydrocarbon solvents.

The U.S. Pat. No. 10,676,685B2 relates to using quaternary nitrogen compounds as a fuel additive and lubricant or kerosene additive to reduce or prevent deposits in injection systems of diesel direct injection engines, to decrease fuel consumption in diesel direct injection engines and to minimize power loss in diesel direct injection engines.

The US patent application US2015/0337227A1 describes a diesel fuel composition comprising a quaternary ammonium salt additive, which encompasses the reaction product of nitrogen species having at least one tertiary amine group and a quaternized agent, wherein the nitrogen specie is selected from: (i) the product reaction of an acylating agent, substituted with hydrocarbyl, and a compound comprising at least one tertiary amine group and one primary amine or alcohol group; (ii) a Mannich reaction product comprising a tertiary amine group; and (iii) a substituted amine, with polyalkylene having at least one tertiary amine group.

In regard to supramolecular compounds derived from ionic liquids or quaternary ammonium salts, it should be mentioned that there are very few related documents, which are described below:

The Chinese patent application CN109879765A is related to an environmentally friendly green solvent, and it is an ionic liquid derived from quaternary ammonium salts, substituted with an adamantane of 10 carbon atoms, and which forms a supramolecular compound with a β-cyclodextrin in a classical host-guest pair. Which have a potential application in supramolecular chemistry.

The Chinese patent CN105964155B is also based on an inclusion compound formed by a quaternized ionic liquid of β-cyclodextrin with an aromatic diamine monomer to prepare a supramolecular polyimide. This product forms an organic polymer membrane to separate and recover acid gases such as $CO_2$ and $H_2S$.

The Chinese patent CN106145168B relates to the preparation of mesoporous alumina using an ionic gel-liquid as a supramolecular template or supramolecular solvent. The ionic liquid at issue is an amino acid derivative such as N-lauryl-L-glutamic acid of n-butylamine.

It is noted that ionic liquids from quaternary ammonium salt were prepared, containing different functional groups, such as hydroxyl, carboxyl, ether and amino, and $Cl^-$, $Br^-$, $I^-$ and $OH^-$ anions to be used as an economical and efficient catalyst, in the synthesis of glycerol carbonate starting from the glycerol transesterification and dimethyl carbonate, without any additional organic solvent and co-catalyst. It was reported that both the cation and the anion of ionic liquids have an important effect on the catalytic activity. Among the ionic liquids, the one that is functionalized with hydroxyl has the highest activity due to the strong interactions between the hydroxyl and the dimethyl carbonate molecule, as well as between the $OH^-$ anion and the glycerol molecule (E. Elhaj, H. Wang, Y. Gu. Molecular Catalysis, 2019, 468, 19-28).

On the other hand, according to state-of-the-art, it is mentioned that supramolecular surfactants are those that are obtained by self-assembly between molecules with surface properties (surfactants). Which promotes changes in the physicochemical properties of each component separately. This allows for getting differentiated chemicals with improved functionality parameters. Compared to a conventional surfactant, a supramolecular surfactant is formed by non-covalent interactions: electrostatic interactions, ion-dipole, dipole-dipole, Van der Waals forces, hydrogen bonding, π-π interactions, charge transfers, which give rise to host-guest interactions (X. Zhang, C. Wang. Chem. Soc. Rev. 2011, 40, 94-101). To prepare a supramolecular surfactant, it is not only necessary to combine two surfactants. Instead, it combines the appropriate hydrophobic and hydrophilic properties to create new amphiphilic characteristics. In other words, it is to modify the amphiphilic features through non-covalent interactions, which allows changing the physicochemical properties of the final product. Based on this, no scientific evidence exists in the literature on using supramolecular surfactants with traceability, marker, or differentiating properties. Therefore, the scientific articles related to quaternary ammonium salts and their supramolecular assemblies are shown below.

R. Dutta et al. has studied the formation of highly stable and ordered supramolecular assemblies using oppositely charged surfactants, in which surface active ionic liquids (SAIL) replace surfactants to form various supramolecular aggregates. The building blocks of supramolecular aggregates (micelle, mixed micelle, and vesicular assemblies) change from pairs of oppositely charged surfactants/surfactants to pairs of surfactants/SAIL and SAIL/SAIL. Likewise, it was found that various biomolecules can also interact with SAILs to build biologically important supramolecular assemblies as drug carriers (R. Dutta, S. Kundu, N. Sarkar. Biophysical Reviews 2018, 10, 861-871).

It is mentioned that also has been examined the nature of amphiphilic self-assembly in protic ionic liquids of alkylammonium (PILs), systematically varying the ionic structure and composition, the hydrogen bonding capacity, and the nanostructure of both PILs and cationic surfactants that form micelles. In this sense, the structure of the micelles for dodecyl ammonium primary quaternary salts in nitrates and thiocyanate of PILs was determined, finding that while the force that determines the solvophobicity depends only on the average polarity of the PIL, surprisingly strong and specific interactions exist of the head group and the counter-ion with the network of hydrogen bonds of the PIL. Said products can be applied as surfactants or nonionic surfactants and in copolymerization principles (A. Dolan, R. Atkin, G. G. Warr). Chem. Sci. 2015, 6,6189-6198).

Additionally, the formation of ionic complexes of di-n-nonylamine with the terminal sulfonic acid of the ionic liquid hydrogen sulfate of 1-(4-sulfobutyl)-3-methylimidazolium has been investigated, which has potential application as electrolytes for the storage- and conversion-energy as supercapacitors and batteries (T. Cherian, D. R. Nunes, T. G. Dane, J. Jacquemin, U. Vainio, T. T. T. Myllymäki, J. V. I. Timonen, N. Houbenov, M. Maréchal, P. Rannou, O. Ikkala. Adv. Funct. Mater. 2019, 1905054).

On the other hand, new compounds have been synthesized whose three-dimensional network structures present numerous hydrogen bonds between bisphosphonate anions, alkylammonium cations, and water molecules. These compounds were obtained by acid reactions (4-amino-1-hydroxybutylidine)-1,1-bis phosphonic (alendronic acid) with organic amines or diamines in a 1:2 or 1:1 ratio in aqueous solution and had pharmaceutical application (G. B. Deacon, C. M. Forsyth, N. B. Greenhill, P. C. Junk. CrystEngComm 2017, 19, 5611-5621).

It is pointed out that ionic pairs and higher-order aggregates of organic ammonium carboxylates exist where the structures of these species are due to isotropic electrostatic interaction and hydrogen bonding between oppositely charged ions. They demonstrated the utility of these salts in the design of supramolecular assemblies such as organogels and higher-order clusters in non-polar solutions (K. Sada, T. Tani, S. Shinkai. SYNLETT 2006, 15, 2364-2374).

Wang et al. investigated the self-assembly of a series of ammonium salts within a single host 18-crown-6, which leads to five supramolecular salts, which are $[(C_4H_6N_3)\cdot(18\text{-crown-}6)_2]^{+\cdot(I_3^-)}$ (1), $[(C_6H_{14}N)\cdot(18\text{-crown-}6)]^{+}\cdot(I_3^-)$ (2), $[(C_6H_{14}N)\cdot(18\text{-crown-}6)]^{+}\cdot(FeCl_4^-)$ (3), $[(C_6H_{10}N_2)\cdot(18\text{-crown-}6)]^{2+}\cdot(ClO_4^-)_2$ (4) and $[(C_6H_8NO_2)\cdot(18\text{-crown-}6)]^{+}\cdot$

[(C₇H₃N₂O₆)⁻]₂ (5). Different types of guest amines were found, this was, varying chain type aliphatic amines, aliphatic ring amines, and aromatic amines, which have a significant impact on the understanding of host-guest interactions and supramolecular architectures (S Wang, X-H Ding, Y-H Li, W Huang. Supramolecular Chemistry 2015, 27, 213-223).

M Zanatta et al. investigated the influence of water traces on the supramolecular organization of the ionic liquids 1,2,3-trimethyl-1H-imidazol-3-ium imidazol-1-ide (MMMI·Im) and 3-n-butyl-1,2-dimethyl-1H-imidazol-3-ium imidazol-1-ide (BMMI·Im). They found that in the solid state, the water molecule is trapped within the ionic lattice through strong hydrogen bonds involving the hydrogens of water and the nitrogens of two imidazolate anions, forming host-guest supramolecular structures, which they maintain to a large extent even in solution with solvents of low and high dielectric constants. These studies allow for rationalizing and predicting the physical and chemical behavior in "wet" ionic liquids (M. Zanatta, A.-L. Girard, G. Marin, G. Ebeling, F. P. dos Santos, C. Valsecchi, H. Stassen, P. R. Livotto, W. Lewis, J. Dupont. Phys. Chem. Chem. Phys. 2016, 18, 18297-18304).

On the other hand, exist different combinations or packages of additives that can be designed or selected to provide a performance improvement. Many of these packages allow differentiation of their hydrocarbon mixtures or fuels and highlight improved characteristics, such as their application in automotive. Among the components of these packages may be a marker or tracer; however, said formulations or compositions do not guarantee that the additives act or can be quantifiable.

As can be seen in the review of state of the art, there are no commercial mixtures or additive compositions for liquid hydrocarbons wherein organic ammonium salts (OAS) or their supramolecular surfactant derivatives (SS) are mentioned that have traceability and detergent dispersant properties against organic scales, which makes the present invention as a novelty.

SUMMARY OF THE INVENTION

The present invention relates to a process for obtaining organic ammonium salts (OAS) and their derivatives, supramolecular surfactants (SS), which simultaneously present the properties of traceability and detergents dispersant of organic scales. Organic ammonium salts (OAS) and their derivatives supramolecular surfactants (SS) have applications as differentiators, markers, or tracers in fuels derived from hydrocarbons; and also to disperse organic scales or inhibit the gums precipitation both in injectors and intake valves of automotive vehicle engines.

Organic ammonium salts (OAS) are obtained through an acid-base reaction between a molecule from the azo family and an amine. Once the OAS is obtained, it reacts with an organic compound (OC) so that through non-covalent interactions, a self-assembly process occurs that gives rise to the SS. Said process is based on green chemistry, that is, in the absence of solvents. These OAS and SS are quantified through the analytical techniques of ultraviolet-visible (UV-VIS) and high-performance liquid chromatography (HPLC) through a calibration curve. Additionally, its performance as a gum-dispersing agent in a single-cylinder engine is evaluated.

Therefore, the present invention clearly exceeds all the indicated references. Having as a purpose to provide new organic ammonium salts (OAS) and their corresponding supramolecular surfactants (SS). Which have traceability and dispersant detergency properties for liquid fuels.

Another purpose is to provide a process for obtaining organic ammonium salts (OAS) and their corresponding supramolecular surfactants (SS) based on green chemistry and whose quantification is carried out through ultraviolet-visible analytical techniques (UV-VIS) and high-performance liquid chromatography (HPLC). An additional purpose of the present invention is to apply organic ammonium salts (OAS) and their corresponding supramolecular surfactants (SS) to differentiate, mark, trace, or dye gasoline or hydrocarbon-derived fuels and disperse organic scale or inhibit the precipitation of gums in injectors, and intake valves of engines of automotive vehicles.

BRIEF DESCRIPTION OF THE DRAWINGS

Drawings that accompany the present invention are described below to have a better understanding of the objects without thereby limiting their scope.

DETAILED DESCRIPTION OF THE INVENTION

Figure 1:
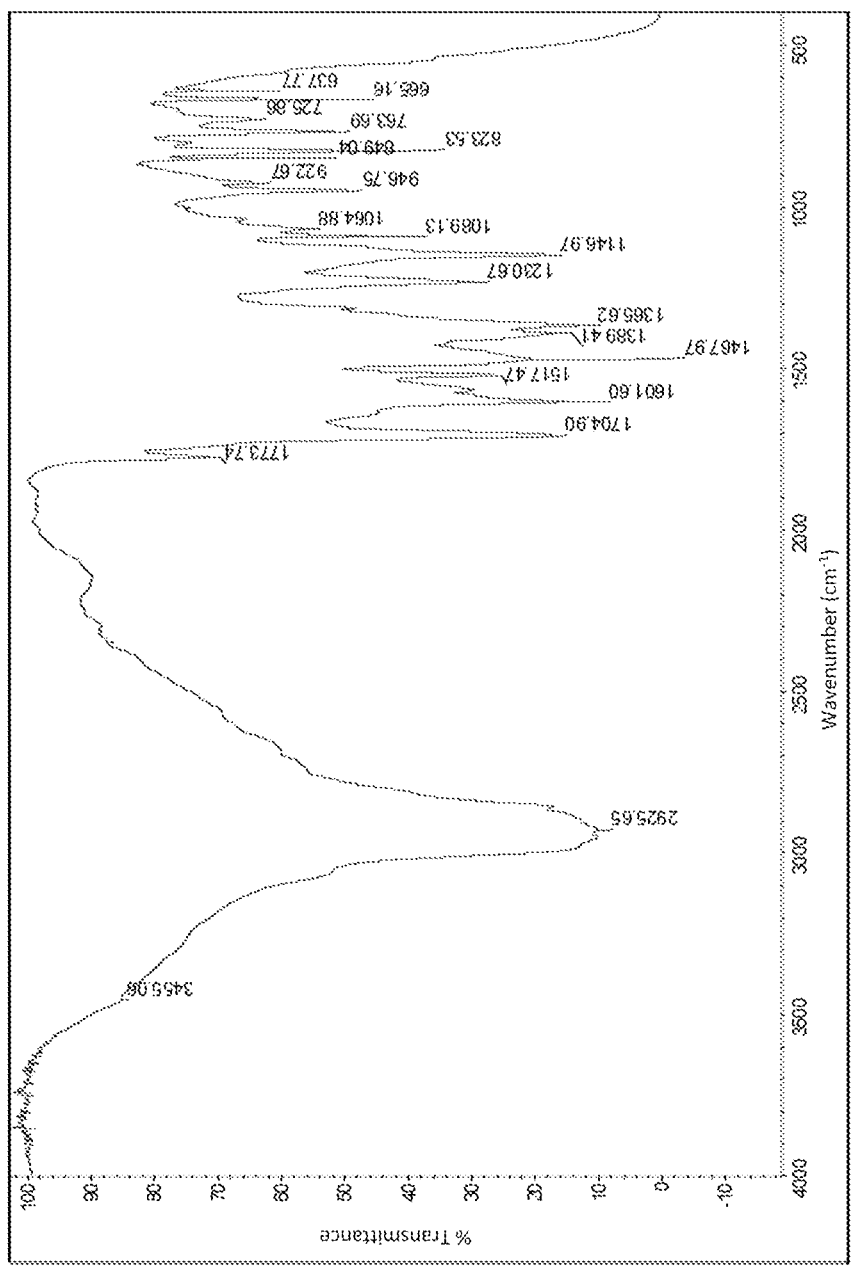
FIG. 1 shows the spectrum and representative FT-IR bands of supramolecular surfactant 1 (SS-1).

The present invention describes the process for obtaining organic ammonium salts (OAS) and their corresponding supramolecular surfactants (SS) derivatives with traceability properties, which can be applied in liquid hydrocarbons as a tracer, marker, differentiator, or dyes. Besides, these organic ammonium salts and their supramolecular surfactant derivatives also function as detergent-dispersant agents of organic deposits (organic scales) and/or gums in storage tanks and pipes, as well as in auto motor vehicles components, such as intake and injection valves. These organic scales typically are generated in liquid hydrocarbons from an olefin compounds polymerization process and organic compounds containing donor atoms or heteroatoms such as nitrogen and sulfur in their structure. And are present in these liquid hydrocarbons, whereby these OAS and SS are ideal for solving the technical problems mentioned before.

Such organic ammonium salts (OAS) and their supramolecular surfactant derivatives (SS) are multifunctional by presenting the following functions: traceability, which permits marking in liquid hydrocarbons; and detergent dispersant of organic scales and gums, which allows having intake and injection valves free of deposits of motor vehicles. Said characteristics made these organic ammonium salts and their supramolecular surfactants derivatives of the present invention novelty and different to additive packs, additive kits, or formulations or synergistic formulations described in the background.

It also is highlighted that through analytic techniques of UV-VIS (ultraviolet-visible spectroscopy) and HPLC (high-performance liquid chromatography), it is feasible to detect and quantify the organic ammonium salts and their supramolecular surfactant derivatives in liquid hydrocarbons object of the present invention, as much as in the absence and presence of additional additives that, traditionally, are added to liquid hydrocarbons. Additional additives may include corrosion inhibitors, demulsifiers, oxygen agents, anti-polymerizers, octane enhancers, detergents, and/or co-detergents. Which ones do not have interference in the quantification of the organic ammonium salts and their supramolecular surfactant derivatives with traceability and detergent dispersant properties. That represents an advantage that permits determining if an additive fuel with organic ammonium salts and/or their supramolecular surfactants has suffered some adulteration type, the object of the present invention.

Organic ammonium salts and/or their supramolecular surfactants can be employed in different fuel types, such as types of gasoline, mixtures of gasoline-ethanol in volume percentages between 0:100 until 99:2, preferably between 80:20 and 95:5; blends of gasoline with methanol or iso-propanol (2-propanol) in % volume gasoline-methanol-iso-propanol ratios from 90:2:8 to 94:1:5, preferably between 90:5:5 to 90:1:4.

The liquid fuels do not need any conditioning, pretreatment, or other preparation to quantify the organic ammonium salts and/or their supramolecular surfactants to be evaluated in this process. Therefore, the detection and quantification process can be done directly in the liquid fuels additived with organic ammonium salts and/or their supramolecular surfactant derivatives, objects of the present invention.

The organic ammonium salts (OAS) of the present invention are the product of an acid-base reaction between an azo compound that contains in its chemical structure protic functional groups, such as acids (carboxylic, sulphonic or similar) and alcohols (AZO type compounds) with amines and/or amino alcohols (A), wherein the acid and protic groups in the azo type compounds (AZO) are preferably selected of the chemical family COOH, SO$_3$H, OH; while the amines (A) can be primary, secondary, and/or tertiary with linear and/or branched hydrocarbon chains and/or with an alkenyl chain from C$_1$ to C$_{32}$ and/or derived from poly-isobutenyl-succinic anhydrides, poly-isobutylene, poly-isobutenylphenols or Mannich bases; and the amino alcohols can be primary, secondary or tertiary, linear or branched, cyclic or aromatic and/or derived from poly-isobutenyl-succinic anhydrides, poly-isobutylene, poly-isobutenylphenols or Mannich bases.

Ammonium salts (OAS) have the general formula AZO:A, which allows them to have the capacity to form intermolecular interactions with organic compounds (CO) that contain heteroatoms or donor atoms in their structure, preferably oxygen, nitrogen, and sulfur: of the chemical families of phenols, oxazolidines, succinimides, imidazolines and naphthols, which, when interacting with AZO type compounds and A type compounds, give rise to their corresponding supramolecular surfactants (SS).

Said supramolecular surfactants are formed through hydrogen bonding, Van der Waals forces, dipole-dipole, ion-dipole, ion-ion, π-π, and π-cation interactions. Providing to the supramolecular surfactant has traceability properties with improved detergency properties and dispersion of organic incrustations and gums.

Organic ammonium salts (OAS) have the general formula AZO:A. Supramolecular surfactants (SS) derived from organic ammonium salts (OAS) and organic compounds (CO) have the general formula OAS:CO in a stoichiometric ratio that can vary from 4:1 to 1:4, preferably in the range from 1:1 to 1:2, where OAS contains the AZO and A groups.

Next, Scheme 2 describes the synthesis route for organic ammonium salts (OAS) consisting of an acid-base reaction between the AZO type compound and the A type compound. And Scheme 3 exposes the synthesis routes corresponding to supramolecular surfactants (SS) with traceability, marker, differentiator, or dye properties that can be used in hydrocarbon-derived liquid fuels and which is based on self-assembly by non-covalent interactions, which gives rise to a surfactant supramolecular.

Scheme 2
Sythesis of organic ammonium salts

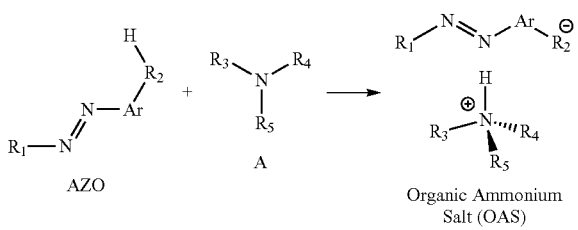

Scheme 3
Synthesis of supramolecular surfactants
derived from organic ammonium salts Route 1

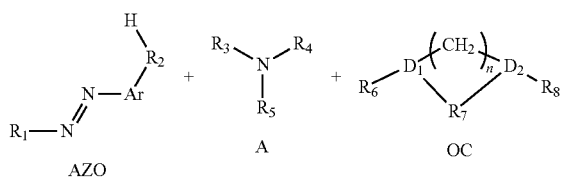

AZO     A     OC

Route 2

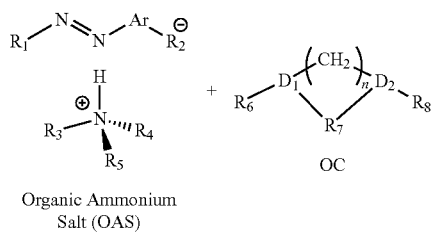

Organic Ammonium
Salt (OAS)     OC

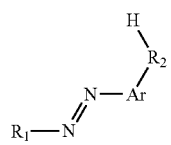

Supramolecular
Surfactant
(SS)

wherein:

An AZO type compound is a compound from the azo family of structural formula (4):

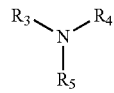 (4)

wherein:

$R_1$: is a linear or branched alkyl or alkenyl chain ranging from $C_1$ to $C_{30}$ or a cycloalkyl or aryl group from $C_5$ to $C_{12}$. It can also be aromatic, benzyls, naphthols, naphthylamines, or dimethyl anilines substituted with electron donors such as $NH_2$, OH, alkyl, and/or electroattractors such as COOR (ester), CO (ketone), COOH, CN, $NO_2$, $SO_3H$;

Ar: is aromatic, such as an aryl, naphthol, naphthylamide, dimethylaniline, indole, pyrrole, pyrazolone, or substituted quinolones groups;

$R_2$: is a substituent of a protic and/or acidic nature, such as COOH, $SO_3H$, OH.

Among the AZO-type compounds (or molecules) that satisfy these conditions are the following: tartrazine (CI acid yellow 23), methyl red, eriochrome black (acid and base form), orange II (CI acid orange 7), Dark Benzo Green B (CI Direct Green I), Congo Red (CI Direct Red 28), Acid Blue 113 (CI Acid Blue 113), Direct Orange 18, Acid Brown 145, Acid Red 183, Methyl Orange, Sudan Red G, Sudan III, DC Red 7, flamingo red, FDC, red 40, carmoisine, sunset yellow, citrus red 2, chocolate brown, PN black, oil red O, metanil yellow, oil orange SS, Sudan IV, amaranth (acid and basic form), orange yellow S, red 2G, tartrazine, bis-azo dyes with acid groups and any other molecule that satisfies the chemical description of the AZO-type molecule, which does not limit the scope of this invention.

Type A compounds are compounds of structural formula (5), which can include primary, secondary, or tertiary amines, or alkyl, cyclic, linear, or branched amino alcohols:

$$R_3\text{-}N(R_4)\text{-}R_5 \quad (5)$$

wherein:

$R_3$: is H or a linear or branched alkyl or alkenyl chain from $C_1$ to $C3_2$, or a cycloalkyl or aryl group from $C_5$ to $C_{12}$. They can also be aromatic groups, such as benzyls, naphthols, naphthylamines, or substituted dimethyl anilines;

$R_4$: is H, or a linear or branched alkyl or alkenyl chain from $C_1$ to $C_{32}$, or a cycloalkyl or aryl group from $C_5$ to $C_{12}$. They can also be aromatic groups, such as benzyls, naphthols, naphthylamines or substituted dimethyl anilines, or groups derived from poly-isobutylene, poly-isobutenyl-succinimides, poly-isobutenyl-amines, poly-isobutenyl-phenols, or poly-isobutenyl-phenol-amines;

$R_5$: can be a linear or branched alkyl or alkenyl chain from $C_1$ to $C_{32}$, or a cycloalkyl or aryl group from $C_5$ to $C_{12}$, or a hydroxyalkyl group, wherein the length of the alkyl group is from $C_2$ to $C_6$.

Organic Compounds (OC) are compounds of structural formula (6) that contain in their chemical structure heteroatoms or donor atoms (D):

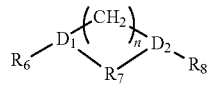 (6)

wherein:

$R_6$: can be hydrogen, or a linear or branched alkyl or alkenyl chain ranging from $C_1$ to $C_{32}$, or a cycloalkyl or aryl group from $C_5$ to $C_{12}$, or substituted aromatic and/or derived from poly-isobutenyl-succinic anhydrides, poly-isobutylene, poly-isobutenylphenols or Mannich bases;

$R_7$: can be a linear or branched alkyl or alkenyl chain ranging from $C_1$ to $C_{32}$, or a cycloalkyl or aryl group from $C_5$ to $C_{12}$, or substituted aromatic;

$R_8$: can be hydrogen, or a linear or branched alkyl or alkenyl chain ranging from $C_1$ to $C_{32}$, or a cycloalkyl or aryl group from $C_5$ to $C_{12}$, or substituted aromatic;

n: can have values between zero and four;

$D_1$: nitrogen with substituents $R_6$ and $R_7$;

$D_2$: can be oxygen, nitrogen, or sulfur as a substituent for the $R_8$ group.

Among the compounds that satisfy the OC characteristics are amino alcohols of the aromatic type, which can be derivatives of aminophenol in its different substitutions, aminonaphthol derivatives, aminoquinoline, amino resorcinol, and aromatic rings with —OH and —$NH_2$ substituents. This is not limited to the families described here but also to their derivatives containing the mentioned characteristics.

The obtention process of the organic ammonium salts (OAS) and their supramolecular surfactants (SS) derivatives from (OAS) of the present invention was carried out according to the following procedures:

Synthesis of OAS: Through an acid-base mass reaction and in the absence of solvents, the stoichiometric quantity in mol of the compounds AZO and A is placed in a reactor, following scheme (2). The reaction occurs at a temperature between 15-100° C., preferably between 20-80° C., with constant mechanical stirring to homogenize the mixture. This process takes approximately 30 minutes to 4 hours, preferably between 1-3 hours.

Synthesis of SS (Route 1): Through a mass reaction and without solvents, the stoichiometric amount in mol of the AZO, A compounds are placed in a reactor. Finally, the organic compound CO is added in a stoichiometric ratio in mol with respect to the AZO compound that can vary from 1:4 to 4:1, preferably in the range from 1:1 to 1:2, following scheme (3). The reaction occurs at a temperature between 15-150° C., preferably between 20-100° C., with constant mechanical stirring to homogenize the mixture. This process takes approximately 30 minutes to 4 hours, preferably between 0.1-3 hours. In the end, a product with the appearance of a paste or a highly viscous liquid is obtained.

Synthesis of SS (Route 2): Through a mass reaction and in the absence of solvents, the stoichiometric amount of the OAS and CO compounds are placed in a reactor with a stoichiometric ratio in mol that can vary from 4:1 to 1:4, preferably in the range from 1:1 to 1:2, following scheme (3). The reaction occurs at a temperature between 15-150° C., preferably between 20-100° C., with constant mechanical stirring to homogenize the mixture. This process takes approximately 30 minutes to 4 hours, preferably between 0.1-3 hours. In the end, a product with the appearance of a paste or a highly viscous liquid is obtained.

No solvents are used during the synthesis of OAS and SS. It is a mass reaction that does not generate byproducts, which makes this process friendly to the environment and is within the field of green chemistry.

Nevertheless, said products can also be obtained in the presence of solvents without affecting the final products' performance and properties. If necessary, the solvents used for these purposes can be polar: primary, secondary, tertiary, or aromatic alcohols; ketone, tetrahydrofuran, dioxane, ethyl acetate, acetic anhydride, and acetonitrile. Solvents can be non-polar: chloroform, pentane, hexane, heptane, octane, cyclohexane, types of gasoline, kerosene, light or heavy aromatic naphtha, benzene, toluene, and xylenes, as well as the corresponding mixtures in any proportion between polar and non-polar. It is not even limited to using water and its combinations with alcohols.

The characterization of the OAS and the SS is carried out through FT-IR spectroscopy, and the shift of the vibration frequencies where the characteristic bands of the functional groups of the AZO, A, and CO type compounds appear, which can be determined supramolecular interactions between these molecules. These displacements have been studied and evidenced in several scientific articles as proof that a supramolecular assembly has occurred (J. Donon, S. Habka, T. Very, F. Charnay-Pouget, M. Mons, D. J. Aitken, V. Brenner, E. Gloaguen. Chem. Phys. Chem. 2021, 22, 2442; S. Habka, T. Very, J. Donon, V. Vaquero-Vara, B. Tardivel, F. Charnay-Pouget, M. Mons, D. J. Aitken, V. Brenner. E. Gloaguen. Phys. Chem. Chem. Phys. 2019, 21, 12798; C. Chi, X. Li, Y. Zhang, L. Li, Z. Wang. Food Funct. 2017, 8, 720; M. Shirakawa, S. I. Kawano, N. Fujita, K. Sada, S. Shinkai. J. Org. Chem. 2003, 68, 5037; MX338862). Also, through the $^1H$ and $^{13}C$ Nuclear Magnetic Resonance technique, supramolecular assemblies can be characterized through the variations in chemical shifts ($\delta$ in ppm) of the corresponding functional groups with respect to the original raw materials, which gives experimental evidence supporting the FTIR finding that supramolecular assembly has occurred (A. Pastor, E. Martinez-Viviente. Coord. Chem. Rev. 2008, 252, 2314; P. S. Denkova, L. Van Lokeren, I. Verbruggen, R. Willem. J. Phys. Chem. B 2008, 112, 10935; M. Pons, P. Bernardo. Supramolecular Chemistry in Encyclopedia of Nuclear Magnetic Resonance, John Wiley & Sons. Ltd. Chichester, 2002, MX338862). Additionally, through UV-VIS, the absorption maximum and the absorptivity coefficient ($\varepsilon$) can be calculated, which is a unique parameter that distinguishes one substance from another. The change in this coefficient $\varepsilon$ is derived from the formation of charge transfer complexes due to supramolecular interactions, which is due to changes in the absorption band's intensity or the displacement of its wavelength (Spectroscopy Studies of Macrocyclic Supramolecular Assembly. 2019 In: Liu Y., Chen Y., Zhang H Y. (eds) Handbook of Macrocyclic Supramolecular Assembly. Springer, Singapore; Analytical Methods in Supramolecular Chemistry 2007. Ed. By C. Schalley, Wiley-VCH).

Examples. The following examples are presented to illustrate the process of obtaining and using organic ammonium salts (OAS) and supramolecular surfactants (SS) that have traceability and dispersant detergency properties for liquid fuels. These examples should not be considered as limiting what is claimed here.

Example 1. Synthesis of the organic ammonium salt, OAS-1. The organic ammonium salt 1 (OAS-1) is prepared through a reaction without solvents. 2 g of methyl red (AZO type compound) and 2 g of oleylamine (type A compound) are placed in a reactor, using the general formula AZO:A for organic ammonium salts in a molar ratio 1:1. It is mixed at 80° C. with mechanical stirring for 30 minutes. The final product (OAS-1) is obtained as a red paste and is soluble in hydrocarbons (7).

The characterization of the organic ammonium salt 1 (OAS-1) derived from this process is shown below:

Representative FT-IR bands ($cm^{-1}$): 3369, 3055, 3002, 2921, 2852, 1599, 1559, 1515, 1465, 1363, 1311, 1247, 1230, 1140, 1089, 1064, 946, 849, 821, 761, 725, 665.

Representative chemical shifts $\delta$ (ppm) in $^1H$ NMR (600 MHZ, $CDCl_3$): 7.79, 7.67, 7.61, 7.33, 7.27, 6.90, 6.58, 5.34, 2.91, 2.44, 1.98, 1.27, 1.20, 1.09, 0.99, 0.87.

Representative chemical shifts δ (ppm) in $^{13}$C NMR (151 MHZ, CDCl$_3$): 174.70, 152.43, 150.02, 143.52, 129.86, 129.83, 128.83, 125.39, 116.72, 111.55, 40.16, 39.73, 31.91, 29.79, 29.76, 29.35, 29.33, 27.24, 22.69, 14.14.

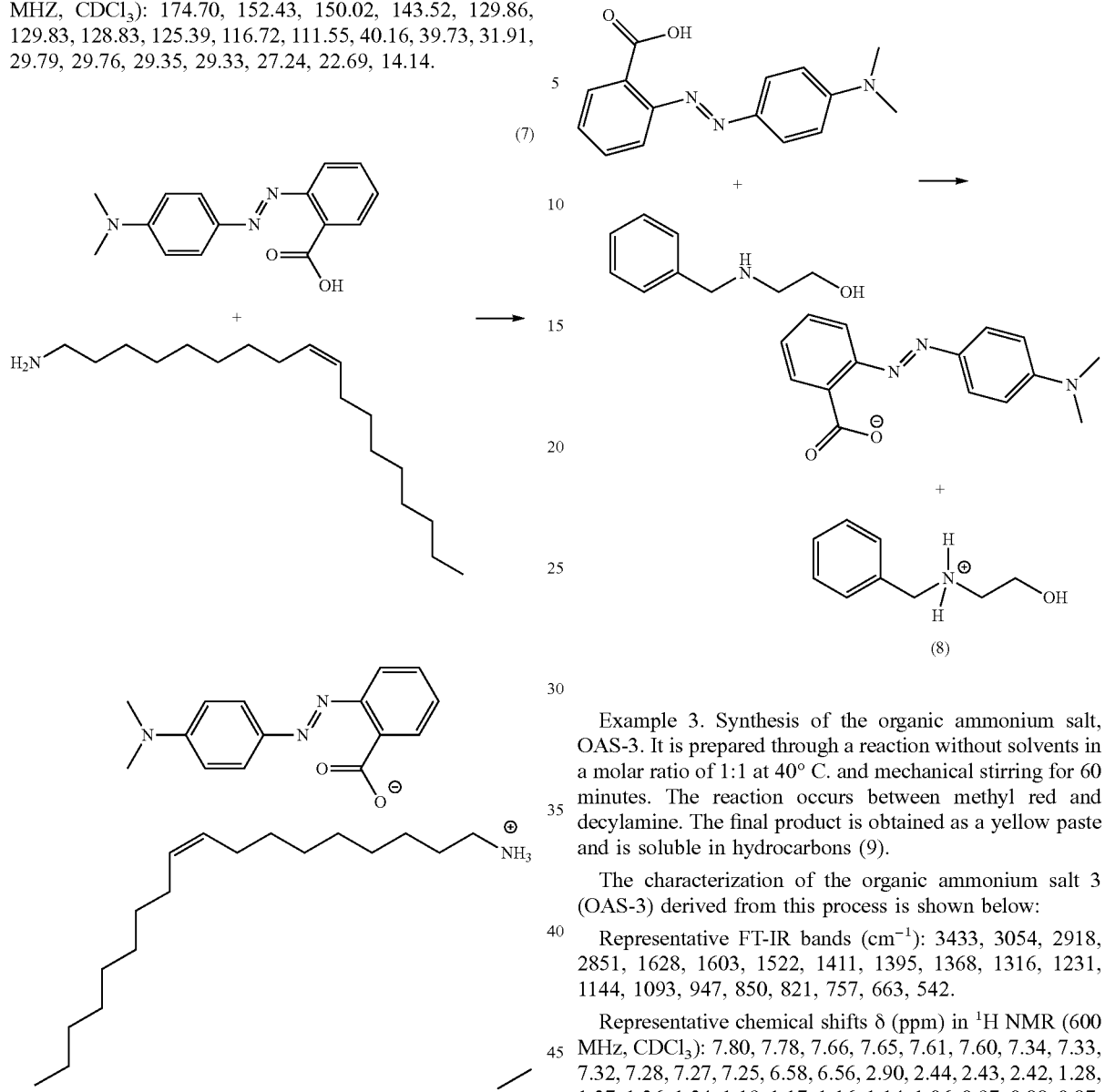

(7)

Example 2. Synthesis of the organic ammonium salt, OAS-2. The organic ammonium salt 2 (OAS-2) is prepared through a reaction without solvents in a molar ratio of 1:1 at 40° C. and mechanical stirring for 60 minutes. The reaction occurs between methyl red and N-benzyl ethanolamine. The final product is obtained as an orange-red paste and is soluble in methanol (8).

The characterization of the OAS-2 derived from this process is shown below:

Representative FT-IR bands (cm$^{-1}$): 3234, 2930, 2796, 2657, 1601 1597, 1451, 1370, 1310, 1239, 1144, 1087, 949, 823, 771, 704, 665.

Representative chemical shifts δ (ppm) in $^1$H NMR (600 MHZ, MeOD): 7.79, 7.74, 7.72, 7.53, 7.52, 7.39, 7.31, 7.25, 7.23, 6.65, 6.63, 3.94, 3.62, 3.20, 2.93, 2.84, 1.17.

Representative chemical shifts δ (ppm) in $^{13}$C NMR (151 MHz, MeOD): 177.54, 154.08, 150.42, 145.02, 140.77, 134.16, 130.70, 130.01, 130.01, 129.97, 129.30, 128.19, 126.28, 117.41, 112.47, 79.44, 58.55, 52.31, 50.17, 40.42.

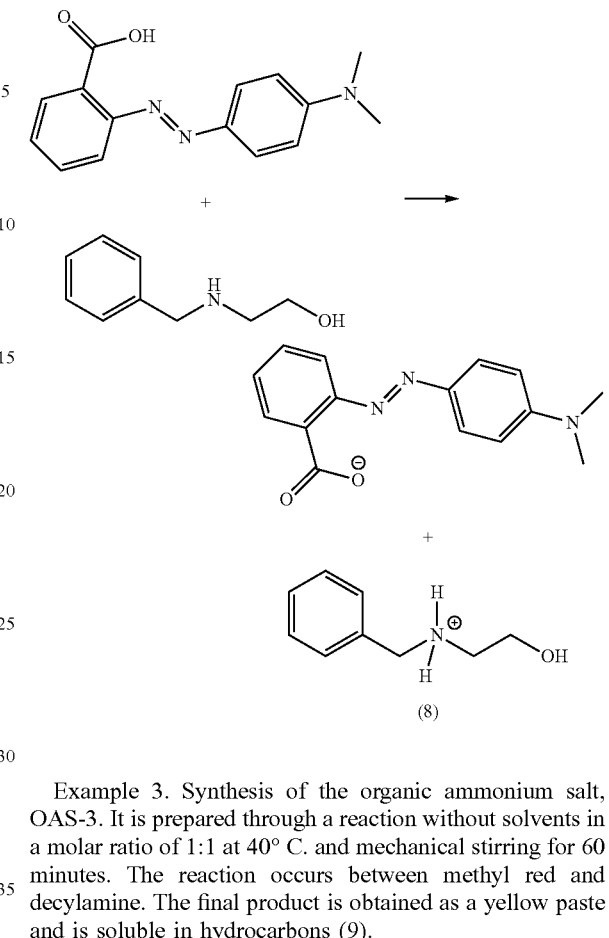

(8)

Example 3. Synthesis of the organic ammonium salt, OAS-3. It is prepared through a reaction without solvents in a molar ratio of 1:1 at 40° C. and mechanical stirring for 60 minutes. The reaction occurs between methyl red and decylamine. The final product is obtained as a yellow paste and is soluble in hydrocarbons (9).

The characterization of the organic ammonium salt 3 (OAS-3) derived from this process is shown below:

Representative FT-IR bands (cm$^{-1}$): 3433, 3054, 2918, 2851, 1628, 1603, 1522, 1411, 1395, 1368, 1316, 1231, 1144, 1093, 947, 850, 821, 757, 663, 542.

Representative chemical shifts δ (ppm) in $^1$H NMR (600 MHz, CDCl$_3$): 7.80, 7.78, 7.66, 7.65, 7.61, 7.60, 7.34, 7.33, 7.32, 7.28, 7.27, 7.25, 6.58, 6.56, 2.90, 2.44, 2.43, 2.42, 1.28, 1.27, 1.26, 1.24, 1.19, 1.17, 1.16, 1.14, 1.06, 0.97, 0.88, 0.87, 0.86, 0.85.

Representative chemical shifts δ (ppm) in $^{13}$C NMR (151 MHZ, CDCl$_3$): 177.86, 152.38, 150.04, 143.56, 128.83, 128.78, 128.24, 125.34, 116.75, 111.54, 40.14, 39.63, 31.92, 29.55, 29.47, 29.30, 29.04, 28.59, 22.70, 14.16.

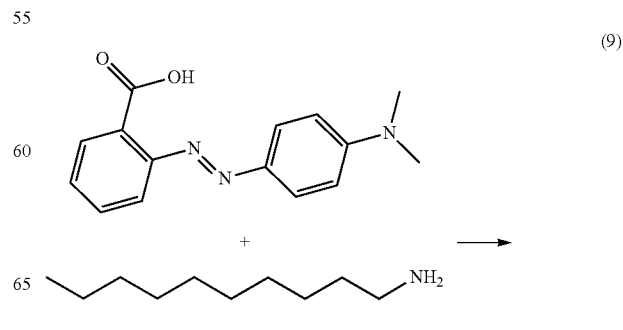

(9)

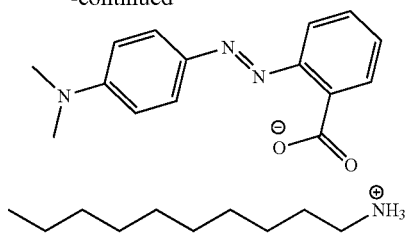

Example 4. Synthesis of the organic ammonium salt, OAS-4. The organic ammonium salt 4 (OAS-4) is prepared through a reaction without solvents in a 1:1 molar ratio at 100° C. and mechanical stirring for 30 minutes. The reaction occurs between methyl red and a hydroxy-ethylamine-ethyl-polyisobutenyl succinimide with an average molecular weight of 1168 Da; organic ammonium salt 4 (OAS-4) is obtained as a dark red paste at room temperature and is soluble in hydrocarbons (10).

The characterization is shown below:

Representative FT-IR bands (cm$^{-1}$): 3489, 2952, 1773, 1704, 1603, 1528, 1468, 1389, 1366, 1312, 1276, 1230, 1165, 1146, 1113, 1086, 943, 889, 818, 764.

Representative chemical shifts δ (ppm) in $^1$H NMR (600 MHZ, CDCl$_3$): (d)8.20, (d)7.90, (d)7.79, (t)7.56, (t)7.46, (d)6.74, (m)5.16, 4.79, 3.65, 3.13, (m)2.92, (m)2.82, 1.41, 1.33, (m)1.10, (m)0.99.

Representative chemical shifts δ (ppm) in $^{13}$C NMR (151 MHZ, CDCl$_3$): 180.22, 177.16, 168.92, 153.71, 150.25, 143.54, 142.29, 139.46, 135.43, 132.59, 131.63, 129.69, 126.65, 115.83, 111.74, 59.88, 59.46, 59.33, 58.77, 58.15, 57.11, 50.97, 50.29, 46.19, 40.30, 39.82, 38.68, 38.10, 38.02, 37.82, 37.73, 37.55, 36.42, 34.22, 32.54, 32.41, 32.40, 31.20, 31.13, 31.12, 30.75, 29.24, 28.98, 18.95, 16.70.

Example 5. Synthesis of the supramolecular surfactant, SS-1. Supramolecular surfactant-1 (SS-1) is prepared through a without-solvents reaction using synthesis route 1. Take 2 g of methyl red (AZO type compound) and 2 g of oleylamine (A type compound) are placed in a reactor in the presence of 8.95 g of an oxazolidine derived from poly alkenyl N-hydroxyalkylsuccinimide with an average molecular weight of 1,000 Da (OC type compound), at 80° C. and mechanical agitation for 30 minutes. The final product (SS-1) contains the AZO, A, and OC molecules with a 1:1:1 molar ratio in their structure. Wherein AZO and A are components of the organic ammonium salt 1 (OAS-1), in such a way that the supramolecular surfactant remains with a formula OAS: OC in a 1:1 molar ratio and it is obtained as a red paste and is hydrocarbons soluble; which also has a supramolecular surfactant structure (11).

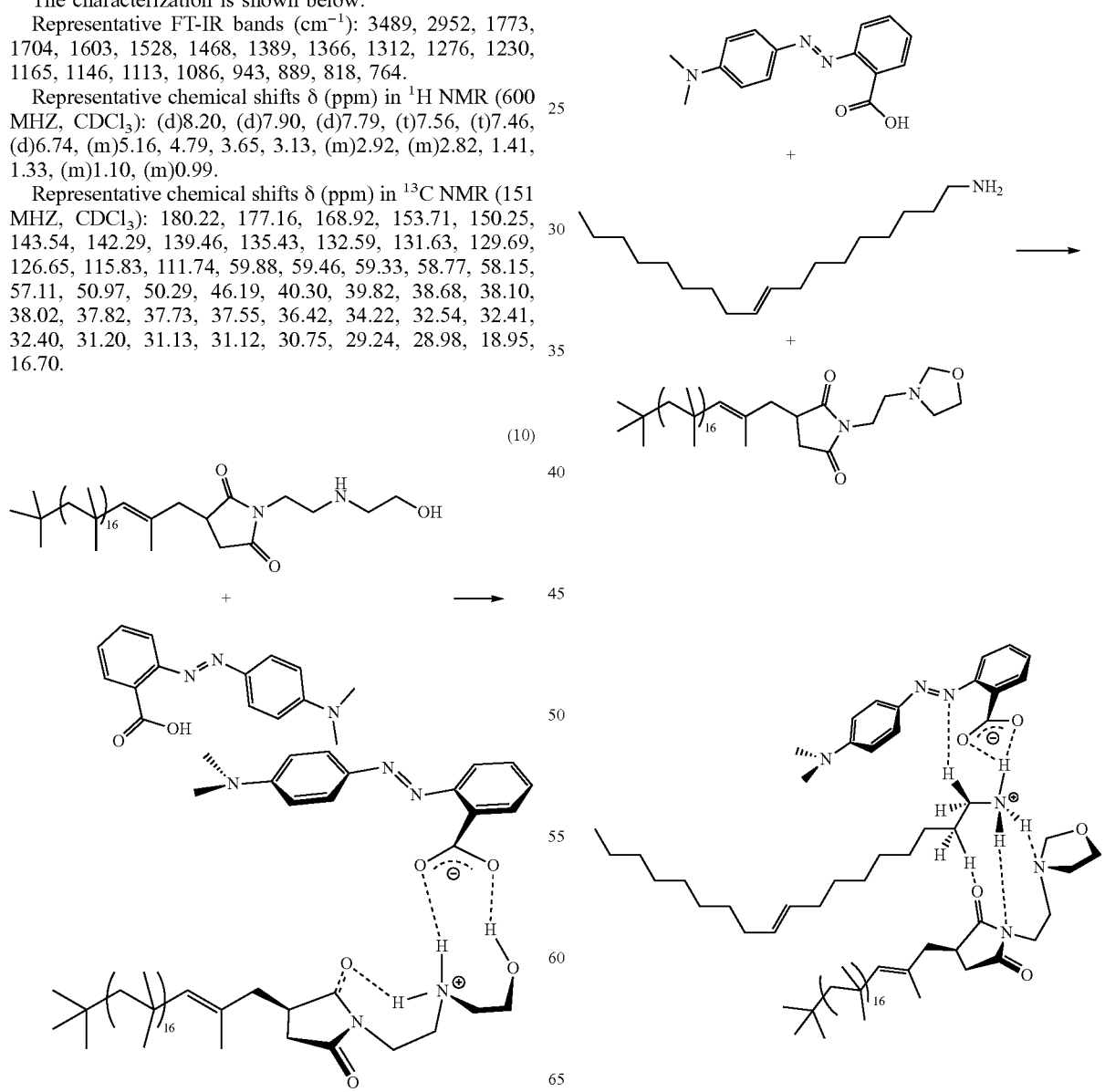

The characterization is shown below:

Representative FT-IR bands (cm$^{-1}$): 3455, 2926, 1774, 1705, 1602, 1517, 1468, 1389, 1366, 1231, 1147, 1089, 947, 849, 764, 665. In the FT-IR spectrum of SS-1 (FIG. 1), the quaternization band of the oleic amine appears at 3455 cm$^{-1}$; in addition, two carbonyl group signals are also observed: the first appear at 1774 cm$^{-1}$ and correspond to succinimide; while the other band appears at 1705 cm$^{-1}$ and corresponds to the methyl red carboxylate group, which is displaced regarding organic ammonium salt 1 (which is discussed in example 1). In such a way, these displacements concerning the original methyl red (1714 cm$^{-1}$) and OAS-1 (1599 cm$^{-1}$) can be deduced that a supramolecular surfactant has been formed that corresponds to SS-1.

Representative chemical shifts δ (ppm) in $^1$H NMR (600 MHZ, CDCl$_3$): (d)7.80, (d)7.67, (td)7.39, (t)7.32, (d)6.63, (m)5.34, 4.83, 4.26, (m)3.64, 3.36, 2.98, 2.89, 2.79, 2.49, 2.39, 2.30, (m)1.99, 1.41, (m)1.28, (m)1.10, (m)0.99.

Representative chemical shifts δ (ppm) in $^{13}$C NMR (151 MHZ, CDCl$_3$): 180.23, 177.16, 173.28, 152.72, 150.08, 143.54, 143.24, 139.45, 135.44130.44, 130.32, 130.18, 130.10, 129.88, 129.82, 129.79, 129.75, 129.03, 128.03, 127.91, 127.88, 127.67, 125.66, 116.50, 115.86, 111.58, 74.64, 59.51, 59.47, 59.33, 59.14, 59.05, 58.77, 58.16, 52.83, 50.94, 50.53, 40.20, 40.00, 39.87, 38.67, 38.21, 38.10, 38.08, 37.98, 37.94, 37.90, 37.83, 37.73, 37.57, 37.05, 36.43, 34.20, 32.62, 32.54, 32.41, 32.28, 31.91, 31.89, 31.77, 31.21, 31.13, 31.08, 31.01, 10.93, 30.73, 29.76, 29.73, 29.69, 29.66, 29.63, 29.60, 29.55, 29.52, 29.49, 29.44, 29.39, 29.36, 29.33, 29.31, 29.25, 29.17, 29.13, 29.11, 29.07, 28.98, 27.58, 27.52, 27.21, 27.18, 26.60, 22.67, 22.55, 14.13, 14.09, 13.73

Figure 2:
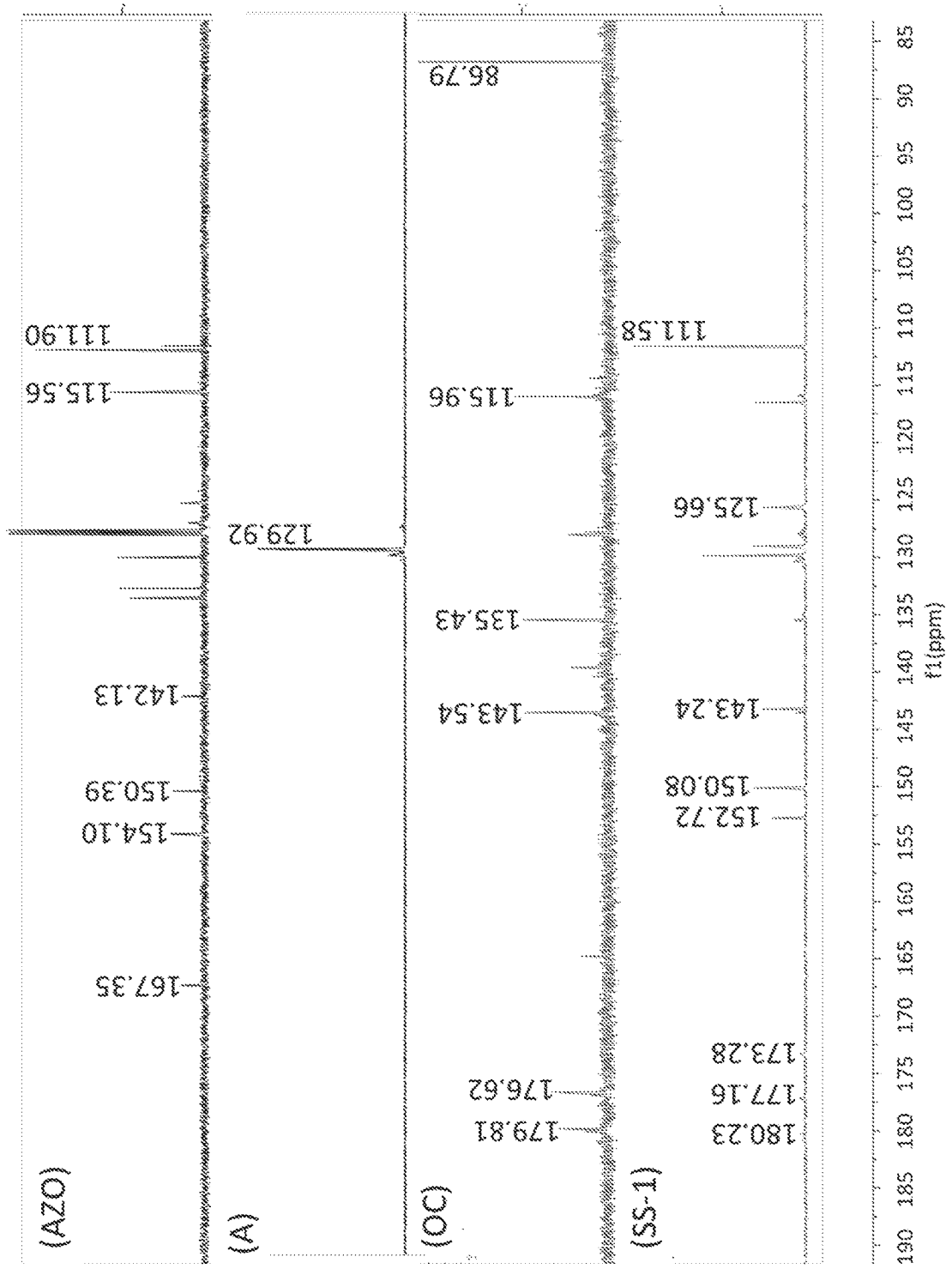
FIG. 2 shows the comparative NMR $^{13}$C (CDCl₃) spectra of methyl red (AZO), oleylamine (A), oxazolidine derived from poly alkenyl N-hydroxyalkyl succinimide (OC), and supramolecular surfactant 1 (SS-1).

In the $^{13}$C NMR spectrum of SS-1 (FIG. 2), three characteristic carbonyl group signals are observed: the first two at 180.23 and 177.16 ppm corresponding to the succinimide fragment of oxazolidine derived from poly alkenyl N-hydroxyalkylsuccinimide (OC), which initially appeared at 179.81 and 176.62 ppm. Also, in SS-1, a third carbonyl signal appears at 173.28 ppm, corresponding to the carbonyl group of methyl red, which is now in the carboxylate form, while in the raw material, it appeared at 167.35 ppm. Additionally, in the spectrum of supramolecular surfactant 1, other displaced signals correspond to the aromatic groups of methyl red since they move from 154.10, 150.39, and 142.13 ppm (in the raw material) to 152.72, 150.08, and 143.24 ppm. These chemical shifts are a consequence of the supramolecular interaction between the components methyl red (AZO), oleylamine (A), and the oxazolidine derived from poly alkenyl N-hydroxyalkylsuccinimide (OC) that give rise to supramolecular surfactant 1 (SS-1).

Example 6. Synthesis of the supramolecular surfactant, SS-2. Supramolecular surfactant 2 (SS-2) was prepared through a without-solvents reaction using synthesis route 2 shown in scheme (3). 3.0000 g of organic ammonium salt 4 (OAS-4) are placed in a reactor, then 2.4730 g of an oxazolidine derived from poly alkenyl N-hydroxyalkylsuccinimide with an average molecular weight of 1,000 Da (OC type compound) are added. The reaction mixture is heated to a temperature of 100° C. and mechanical stirring for 30 minutes. The final product (SS-2) has a formula OAS:OC with a 1:1 molar ratio and contains the AZO, A, and OC molecules in a 1:1:1 ratio. SS-2 is obtained as a paste at room temperature and is soluble in hydrocarbons, which shows a supramolecular assembly (12).

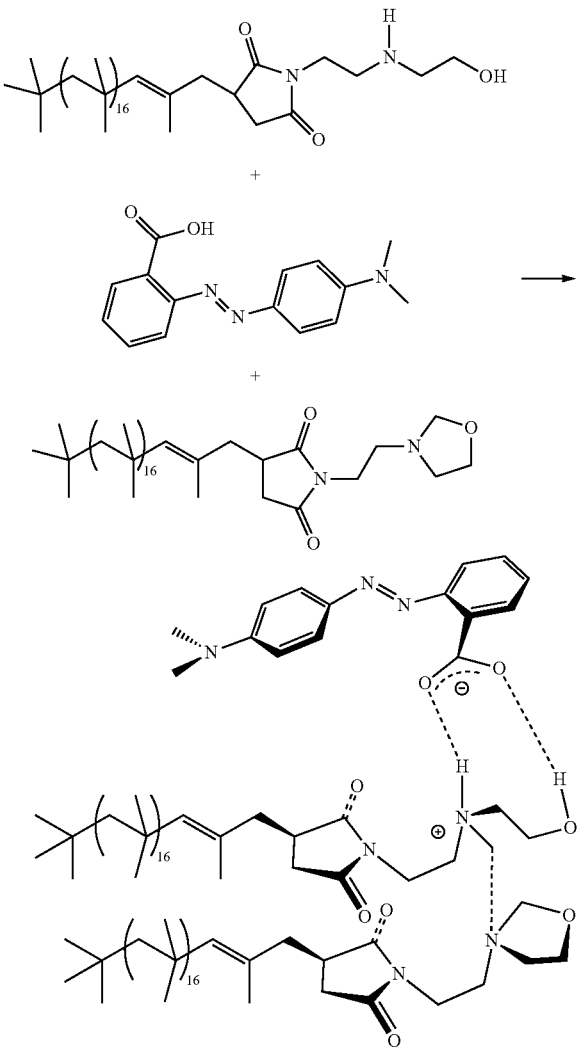

(12)

Figure 3:
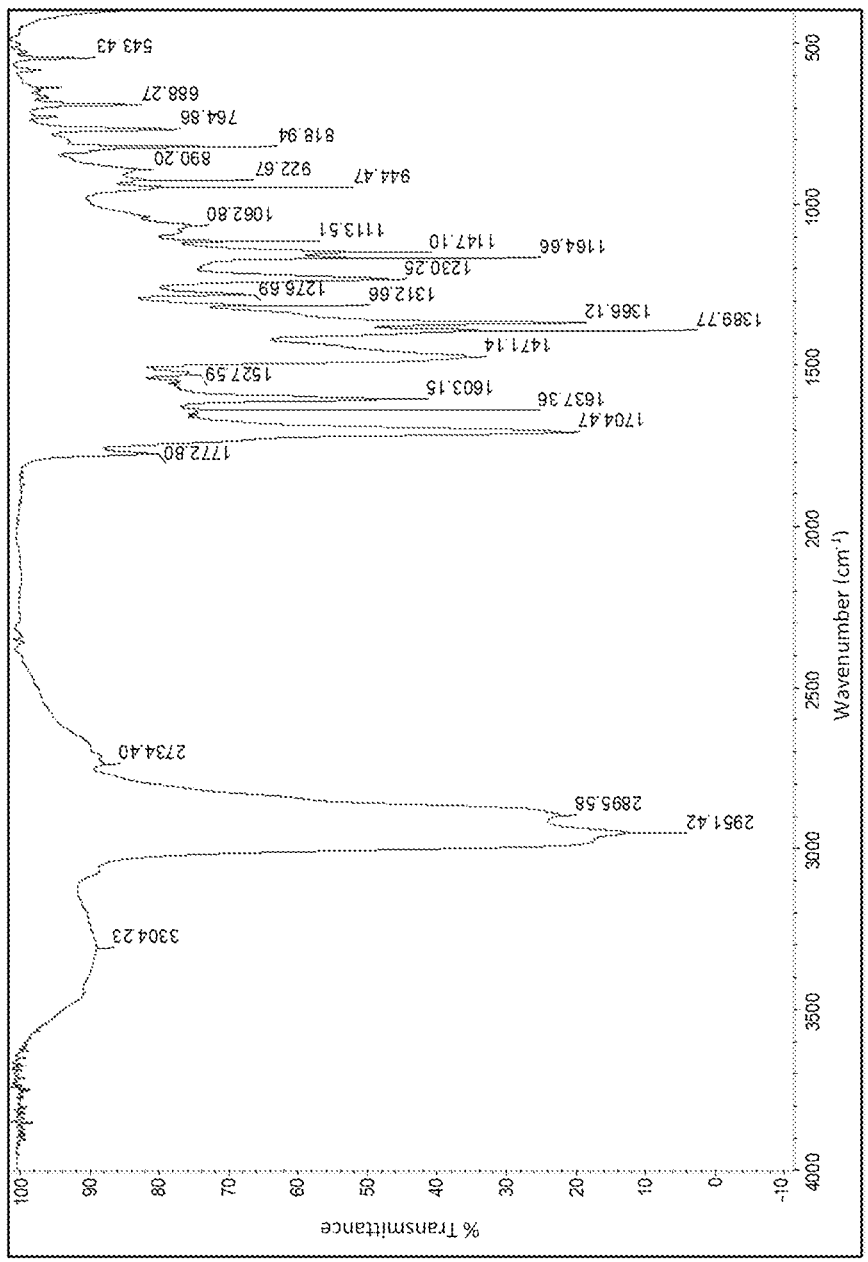
FIG. 3 presents the spectrum and representative FT-IR bands of supramolecular surfactant 2 (SS-2).

The characterization is shown below:

Representative FT-IR bands (cm$^{-1}$): 3304, 2951, 1896, 2734, 1773, 1704, 1603, 1528, 1471, 1390, 1366, 1277, 1230, 1165, 1147, 819, 765, 688. In the FT-IR spectrum (FIG. 3) of supramolecular surfactant 2 (SS-2), the band corresponding to —OH is observed at 3304 cm$^{-1}$. If we compare this band with the same one from OAS-4 that appeared at 3489 cm$^{-1}$, it can be seen that it moves. It is important to note that Organic Ammonium Salt 4 (OAS-4) is a precursor of Supramolecular Surfactant 2 (SS-2); therefore, the difference is that Quaternary Salt 4 has a supramolecular assembly. Other displaced bands appear at 1773 and 1704 cm$^{-1}$ corresponding to the carbonyl groups of hydroxy-ethylamine-ethyl poly alkenyl succinimide (A) and oxazolidine derived from poly alkenyl N-hydroxyalkylsuccinimide (OC).

Representative chemical shifts δ (ppm) in $^1$H NMR (600 MHZ, CDCl$_3$): (d)8.20, (d)7.90, (d)7.79, (t)7.56, (t)7.46, (d)6.74, (m)5.16, 4.79, 3.65, 3.13, (m)2.92, (m)2.82, (m)1.41, (m)1.33, (m)1.10, (m)0.99.

Figure 4:
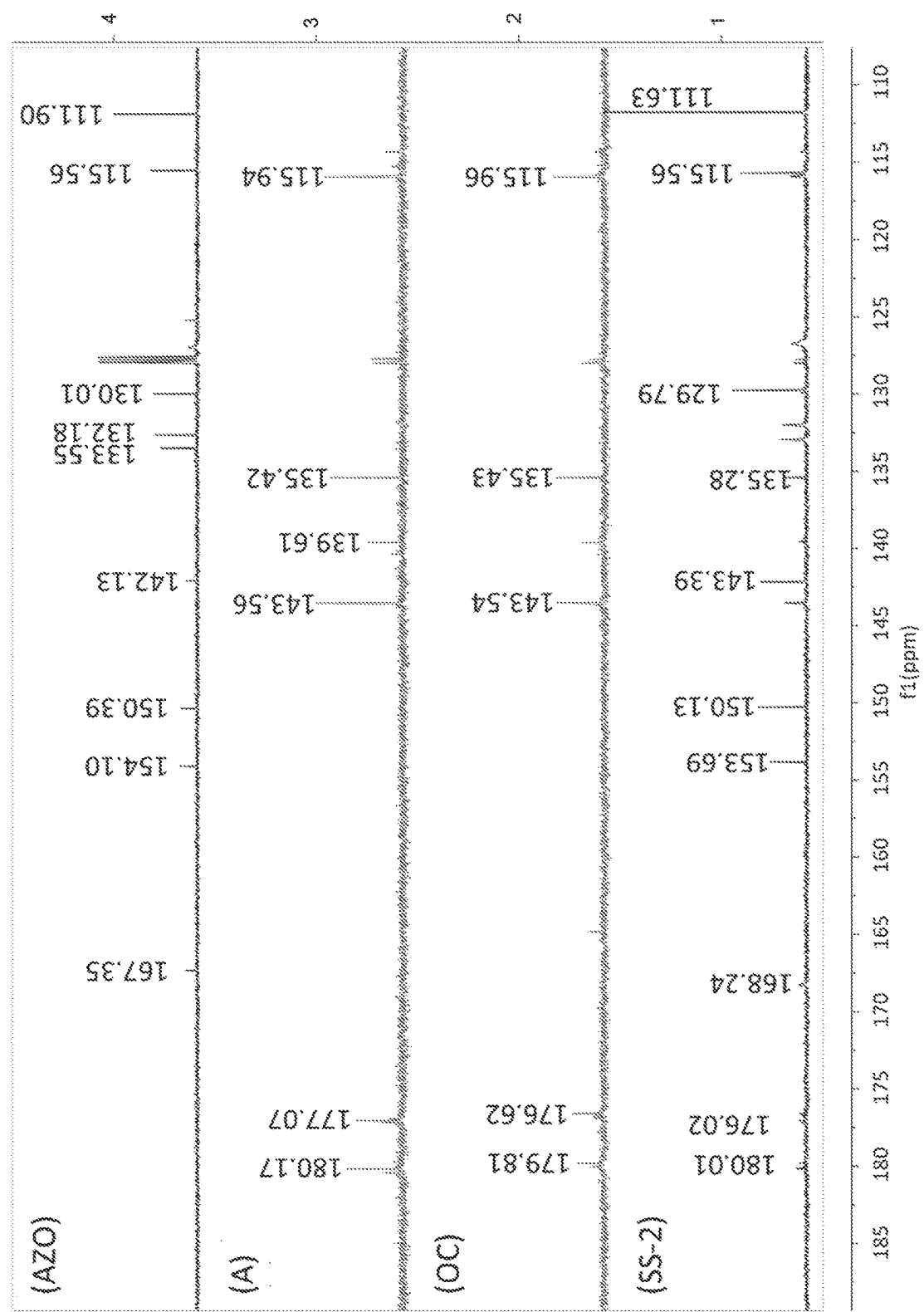
FIG. 4 shows representative $^{13}$C NMR (CDCl₃) spectra of methyl red (AZO), hydroxy-ethylamine-ethyl poly alkenyl succinimide (A), the oxazolidine derived from poly alkenyl N-hydroxyalkyl succinimide (OC), and supramolecular surfactant 2 (SS-2).

Representative chemical shifts δ (ppm) in $^{13}$C NMR (151 MHZ, CDCl$_3$): 180.01, 176.02, 168.24, 153.69, 150.13, 143.39, 142.29, 139.46, 135.28, 132.59, 131.63, 129.79, 126.65, 115.83, 111.63, 59.88, 59.46, 59.33, 58.77, 58.15, 50.97, 50.29, 46.19, 40.30, 38.10, 38.02, 36.42, 34.22, 32.40, 31.20, 31.13, 31.12, 30.75, 29.74, 28.98, 18.95. In the $^{13}$C NMR spectrum of SS-2 (FIG. 4), three carbonyl signals are observed at 180.01 and 176.02 ppm that correspond to the carbonyls of the succinimide groups of A and OC type compounds; the third carbonyl signal appears at 168.24 ppm corresponding to the carboxylate group of the AZO type molecule. Initially, these signals appeared in the corresponding raw materials with different chemical shifts: 180.17 and 177.07 ppm for the A type compound and 179.81 and 176.62 ppm for the Ar type compound. The displacement of the carbonyl signal of methyl red (AZO type compound) is also observed since it appeared as the carbonyl of a carboxylic acid at 167.35 ppm, and in the quaternary salt, it seems to carboxylate at 168.24 ppm. In addition, shifts are observed in the aromatic signals that appear between 154-130 ppm in methyl red (AZO type compound), and in quaternary salt 4, these signals also appear shifted. These displacements confirm what was observed in FT-IR and show that quaternary salt 4 has a supramolecular assembly.

Example 7. Synthesis of the supramolecular surfactant, SS-3. Supramolecular surfactant 3 (SS-3) is prepared through a reaction without solvents using the synthesis route 2 of the scheme (3). 4.0000 g of organic ammonium salt 1 (OAS-1) are placed in a reactor, then 0.6989 g of phenol (OC type compound) is added. The reaction mixture is brought to a temperature of 40° C. and mechanical stirring for 30 minutes. The final product (SS-3) has a formula SAO:OC with a 1:1 molar ratio and contains the AZO, A, and OC molecules in a 1:1:1 ratio. SS-3 is obtained as a highly viscous liquid at room temperature and is soluble in hydrocarbons, which shows a supramolecular assembly similar to (12).

Figure 5:
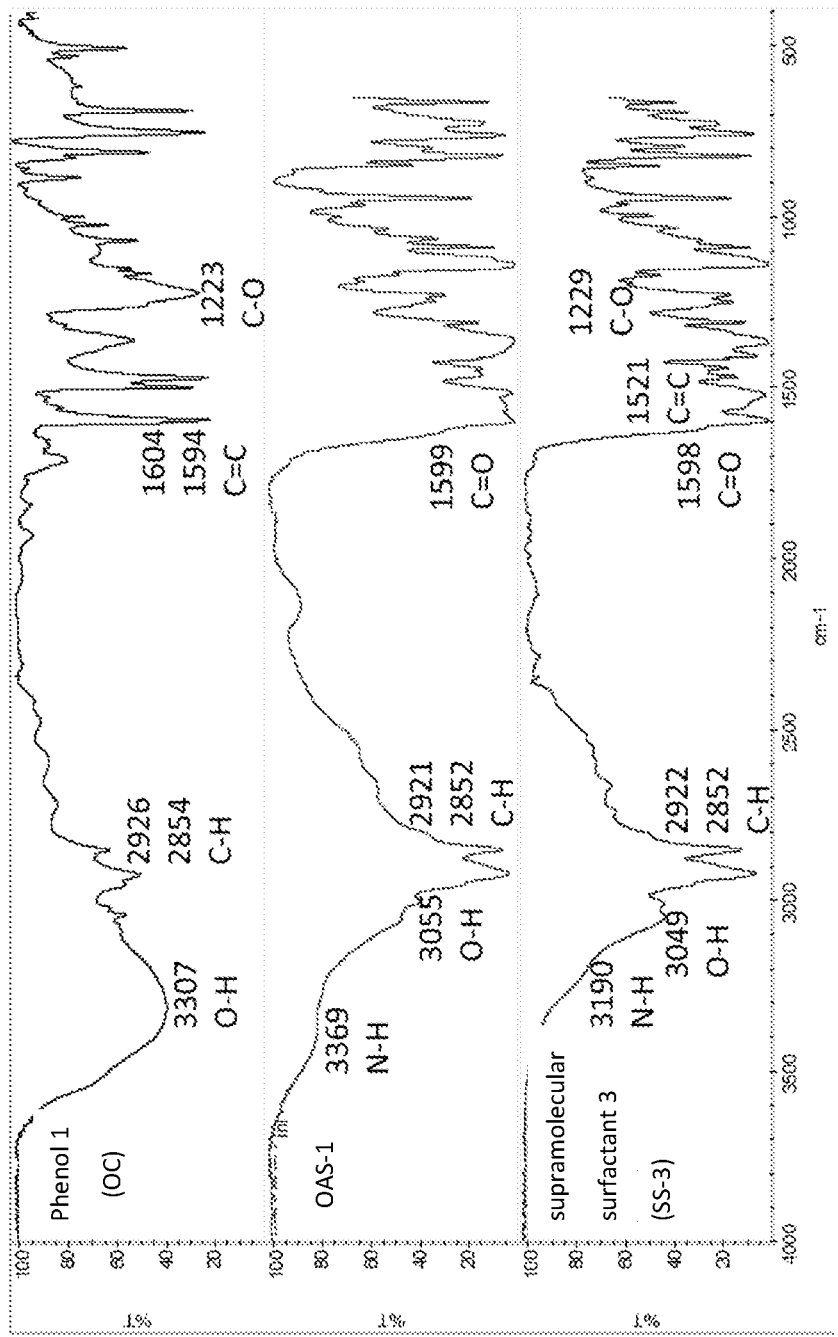
FIG. 5 illustrates the comparative FT-IR spectra and bands of phenol (OC), organic ammonium salt 1 (OAS-1), and supramolecular surfactant 3 (SS-3).

Representative FT-IR bands (cm$^{-1}$): 3190, 3049, 3011, 2922, 2852, 1598, 1521, 1468, 1406, 1365, 1309, 1250, 1139, 1089, 1033, 946, 852, 823, 759, 695, 666. In the FT-IR spectrum of SS-3 (FIG. 5), two bands that appear at 3190 and 3049 cm$^{-1}$ are observed and correspond to the N—H (ammonium) and —OH groups, respectively. On the one hand, the —OH band in phenol (OC) originally appeared at 3307 cm$^{-1}$, and in SAO-1, these bands appeared at 3369 and 3055 cm$^{-1}$, respectively. The displacement of these bands in SS-3, concerning the signals in the raw materials, is evidence of the supramolecular interactions of the product.

Representative chemical shifts δ (ppm) in $^1$H NMR (600 MHZ, CDCl$_3$): 7.78, 7.76, 7.70, 7.69, 7.65, 7.64, 7.35, 7.06, 7.05, 6.76, 6.75, 6.57, 5.56, 5.34, 5.33, 2.92, 2.45, 2.44, 2.43, 2.01, 2.00, 1.96, 1.95, 1.27, 1.27, 1.22, 1.21, 1.09, 1.08, 0.98, 0.97, 0.87, 0.86.

Figure 6:
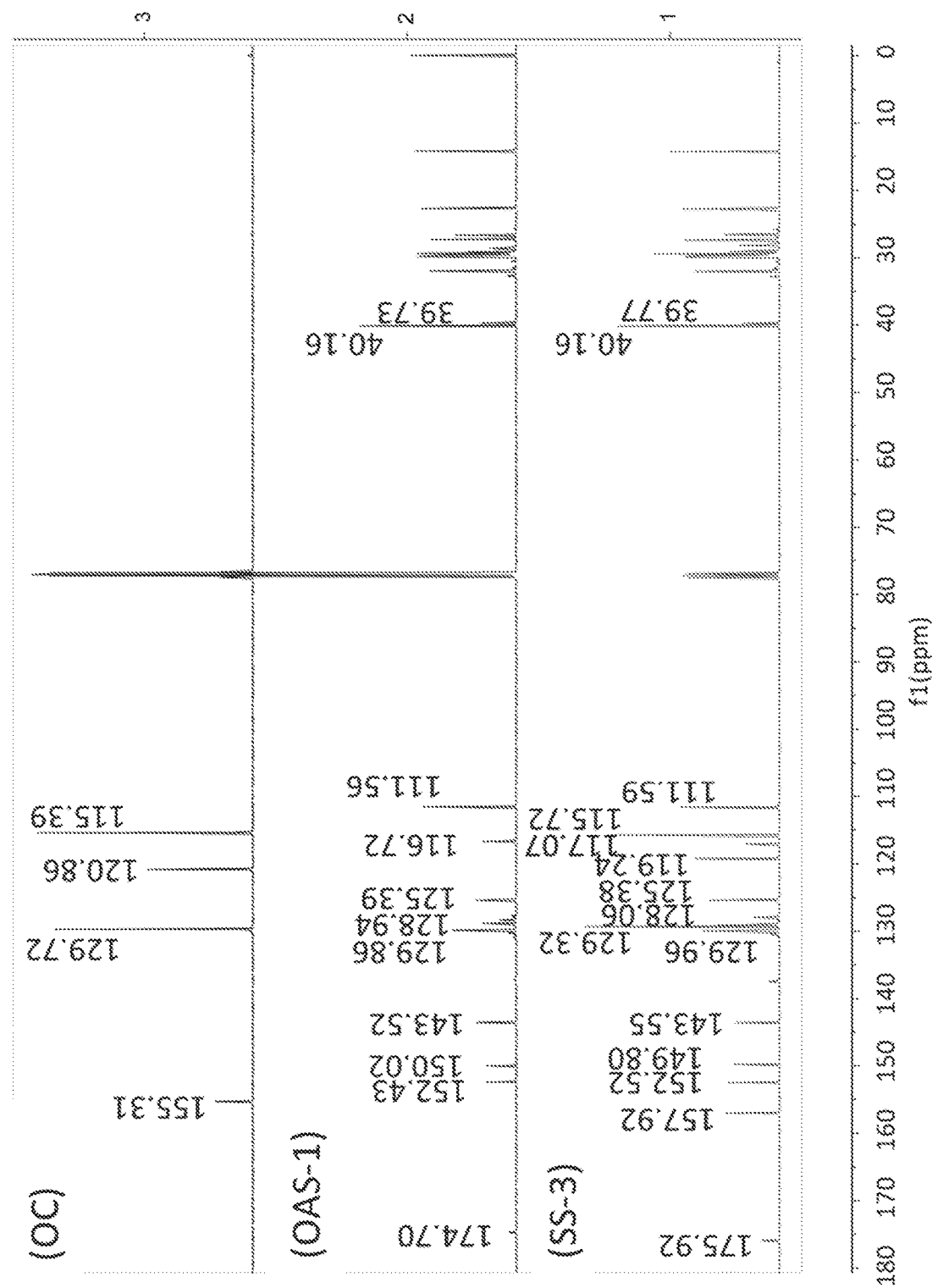
FIG. 6 shows representative chemical shifts in δ (ppm) in $^{13}$C NMR (CDCl₃) of phenol (OC), organic ammonium salt 1 (OAS-1), and supramolecular surfactant 3 (SS-3).
Figure 7:
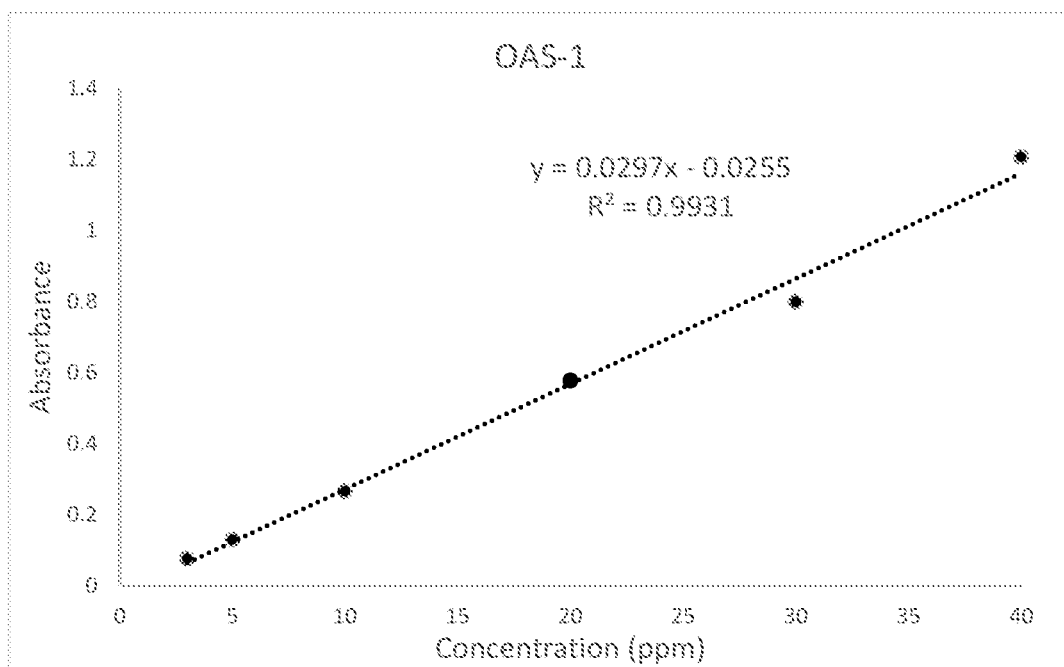
FIG. 7 shows the calibration curve, $A_{max}$ vs. concentration of organic ammonium salt 1, OAS-1.
Figure 8:
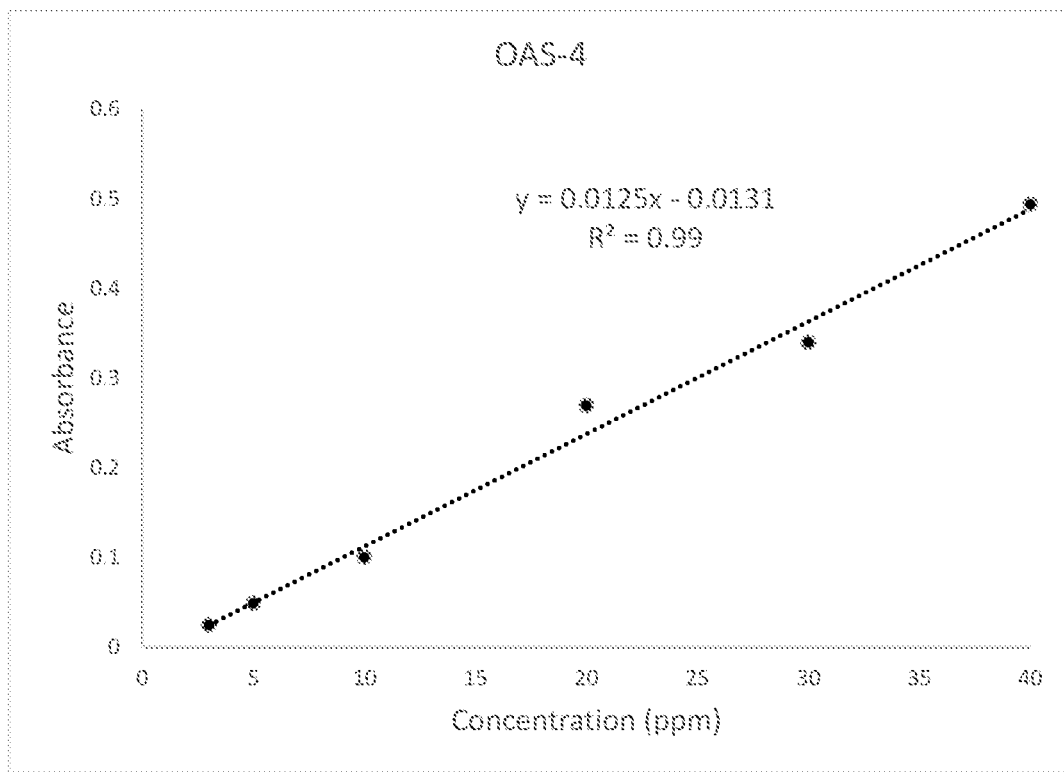
FIG. 8 shows the calibration curve, $A_{max}$ vs. concentration of organic ammonium salt 1, OAS-4.
Figure 9:
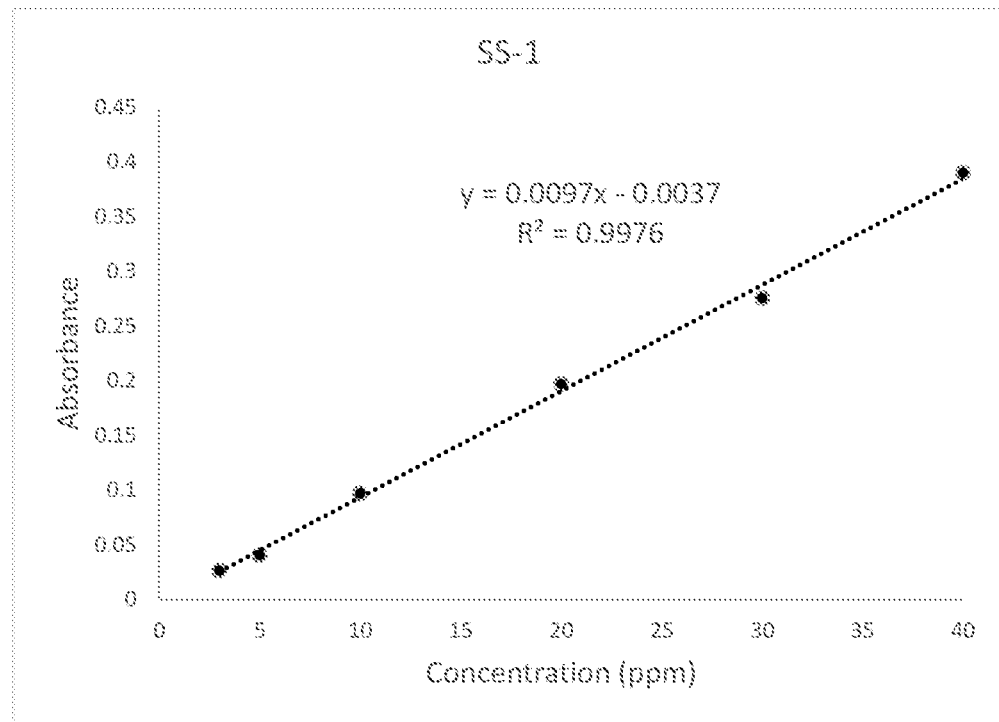
FIG. 9 illustrates the calibration curve, $A_{max}$ vs. concentration of supramolecular surfactant SS-1.
Figure 10:
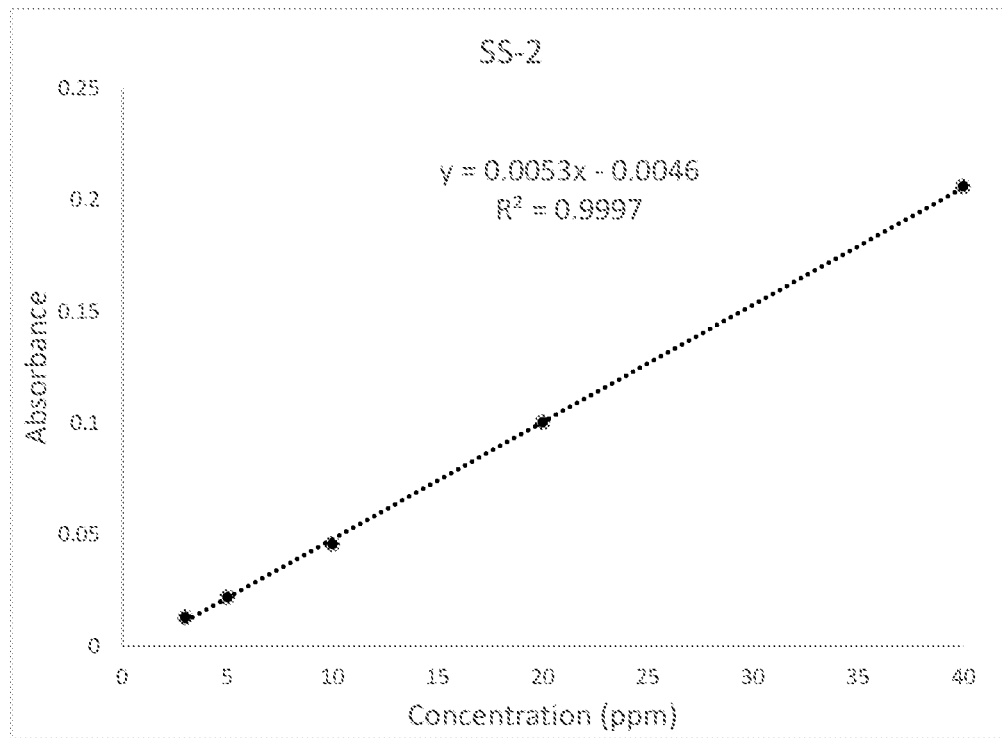
FIG. 10 exhibits the calibration curve, $A_{max}$ vs. concentration of supramolecular surfactant SS-2.
Figure 11:
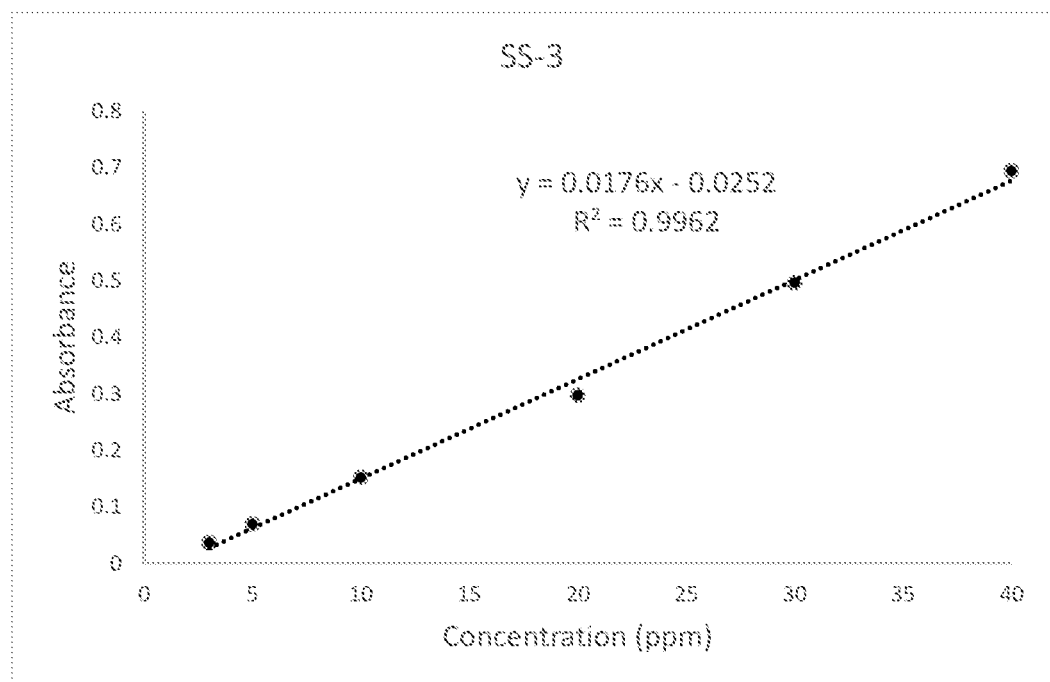
FIG. 11 shows the calibration curve, $A_{max}$ vs. concentration of supramolecular surfactant SS-3.

Representative chemical shifts δ (ppm) in $^{13}$C NMR (151 MHZ, CDCl$_3$): 175.92, 157.92, 152.50, 149.80, 143.55, 135.99, 129.96, 129.32, 129.48, 129.30, 129.04, 128.06, 125.38, 119.24, 117.07, 115.72, 111.59, 40.16, 39.77, 31.90, 29.78, 29.75, 29.54, 29.37, 2934, 29.32, 29.24, 28.98, 28.98, 28.49, 27.23, 26.49, 22.68, 14.13. In the $^{13}$C NMR spectrum of SS-3 (FIG. 6), a signal is observed at 175.92 ppm corresponding to the AZO compound's carboxylate group into the organic ammonium salt 1 (OAS-1). That same signal appears at 174.70 ppm in the OAS-1 spectrum, which shows that this carboxylate group has shifted its signal and participates in a supramolecular interaction. On the other hand, the four aromatic phenol (OC) aromatic signals initially appear at 155.31, 129.72, 120.86, and 115.39 ppm, and in the spectrum of SS-3, they appear displaced at 157.92, 129.32, 119.24, and 115.72 ppm, respectively. These displacements indicate that the aromatic part of phenol (OC) is forming x-type interactions with quaternary ammonium salt 1 (OAS-1) to give rise to the formation of supramolecular surfactant 3 (SS-3).

Example 8. Determination of traceability properties through UV-VIS spectroscopy. The traceability property of some prepared organic ammonium salts (OAS) and supramolecular surfactants (SS) were evaluated. This is done through the UV-VIS technique, using gasoline as a solvent. The procedure consists of building the calibration curve of each material to be analyzed. Later, through the absorbance reading of a test sample, the absorbance value is interpolated in said calibration curve to know the concentration of the substance with traceability properties.

Equipment: UV-VIS spectrophotometer, magnetic stirrer, and analytical balance.

Materials: Volumetric flasks, volumetric pipettes, glass vials, and quartz cells with a light path length of 1 cm.

Sample to analyze: Organic ammonium salt (OAS), supramolecular surfactant (SS), solutions of known concentration of the mentioned products dissolved in regular gasoline.

Test Procedure:
a) In a 100 mL volumetric flask, prepare a standard solution at 10 000 ppm of the product to be analyzed. To do this, 0.0250 g of OAS or SS is weighed and later placed in a 25 mL volumetric flask, and regular gasoline is used as a solvent to reach the volume graduation mark.
b) An aliquot of the standard solution is taken and diluted in regular gasoline to obtain at least five or more solutions in concentrations ranging from 0.5 ppm to 100 ppm.
c) Next, in the UV-VIS spectrophotometer and using a quartz cell, the UV-VIS spectrum of each sample is obtained in a spectral window from 350 to 600 nm.
d) In each UV-VIS spectrum, the absorbance maximum ($A_{max}$) and the wavelength at which this occurs (maximum absorption wavelength, $\lambda_{max}$) are determined. With these $A_{max}$ values, a calibration curve of absorbance as a function of concentration ($A_{max}$ vs. concentration) is built, representing a straight line that must comply with the Lambert-Beer law.
e) With the calibration curve, the specific absorptivity constant (ε) is calculated at the maximum absorption wavelength value ($\lambda_{max}$). The slope of the linear fit equation corresponds to the value of the specific absorptivity constant (ε). The calibration curve is done for each OAS and SS to be analyzed.

FIGS. 7, 8, 9, 10, and 11 show the linear range of absorbance as a function of the concentration of some OAS and SS, which demonstrates that organic ammonium salts (OAS) and supramolecular surfactants (SS) of the present invention can be detected as tracers, dyes, markers or differentiators in fuels in concentrations ranging from 0.5 ppm onwards, through the UV-VIS spectroscopy technique.

Table 1 shows the values obtained for the specific absorptivity constant of the ammonium salts OAS-1 and OAS-4 and the supramolecular surfactants SS-1, SS-2, and SS-3.

TABLE 1

| Product | $\lambda_{max}$ (nm) | Specific absorptivity constant, ε (mL · g$^{-1}$ · cm$^{-1}$) |
|---|---|---|
| OAS-1 | 461 | 29.7 |
| OAS-4 | 464 | 12.5 |
| SS-1 | 461 | 9.7 |

TABLE 1-continued

| Product | $\lambda_{max}$ (nm) | Specific absorptivity constant, $\varepsilon$ (mL · g$^{-1}$ · cm$^{-1}$) |
|---|---|---|
| SS-2 | 460 | 5.3 |
| SS-3 | 461 | 17.6 | f) Determination of the concentration of a test sample. To show that it is feasible to determine the concentration of OAS and SS in gasoline through the determination of absorbance through the UV-Vis spectroscopy technique and the use of the generated equations, it was prepared for the case of the products OAS-1, OAS-4, SS-1, SS-2 and SS-3 a sample in Mexican gasoline of the PEMEX-Magna type free of additives with a known concentration, or of reference, at 10 ppm; subsequently, its absorbance was determined at the wavelength established in Table 2 ($\lambda_{max}$), and the concentration of product in each of the test samples were calculated though the corresponding equation. The obtained absorbance values ($A_{max}$) and the calculated concentrations for the products OAS-1, OAS-4, SS-1, SS-2, and SS-3 are shown in Table 2.

The comparison of the absorbance value obtained against that calculated for the products OAS-1, OAS-4, SS-1, SS-2, and SS-3 shows that the absolute maximum error obtained is 4.3% (less than 5%), which confirms that the procedure through UV-VIS spectroscopy allows to reliably quantify the concentration of organic ammonium salt (OAS) and supramolecular surfactant (SS) in gasoline.

TABLE 2

| Product | $A_{max}$ | Concentration found (ppm) | Error % respect to the reference concentration |
|---|---|---|---|
| OAS-1 | 0.2763 | 10.16 | 1.6 |
| OAS-4 | 0.1119 | 10 | 0 |
| SS-1 | 0.0971 | 10.39 | 3.9 |
| SS-2 | 0.0507 | 10.43 | 4.3 |
| SS-3 | 0.1501 | 9.96 | 1.19 |

Example 9. Determination of traceability properties through high-performance liquid chromatography. The High-Performance Liquid Chromatography (HPLC) technique can also determine the traceability property so that a calibration curve must be built at different concentrations of the substance to be determined, in this case, OAS or SS. Later, this calibration curve is then used to determine the OAS or SS concentration in unknown or test samples.

Equipment: High-performance liquid chromatograph (HPLC) with diode array detector and Nova-Park HR C18 column, 6 µm, 60 Å, 3.9×300 mm; analytical balance.

Solvents: Acetonitrile and methanol (mobile phase), regular gasoline.

Materials: Volumetric flasks, volumetric pipettes, glass vials and micropipettes, magnetic stirrer.

Sample to analyze: Organic ammonium salt (OAS) or supramolecular surfactant (SS). Solutions of known concentration of the mentioned products dissolved in regular gasoline.

Figure 12:
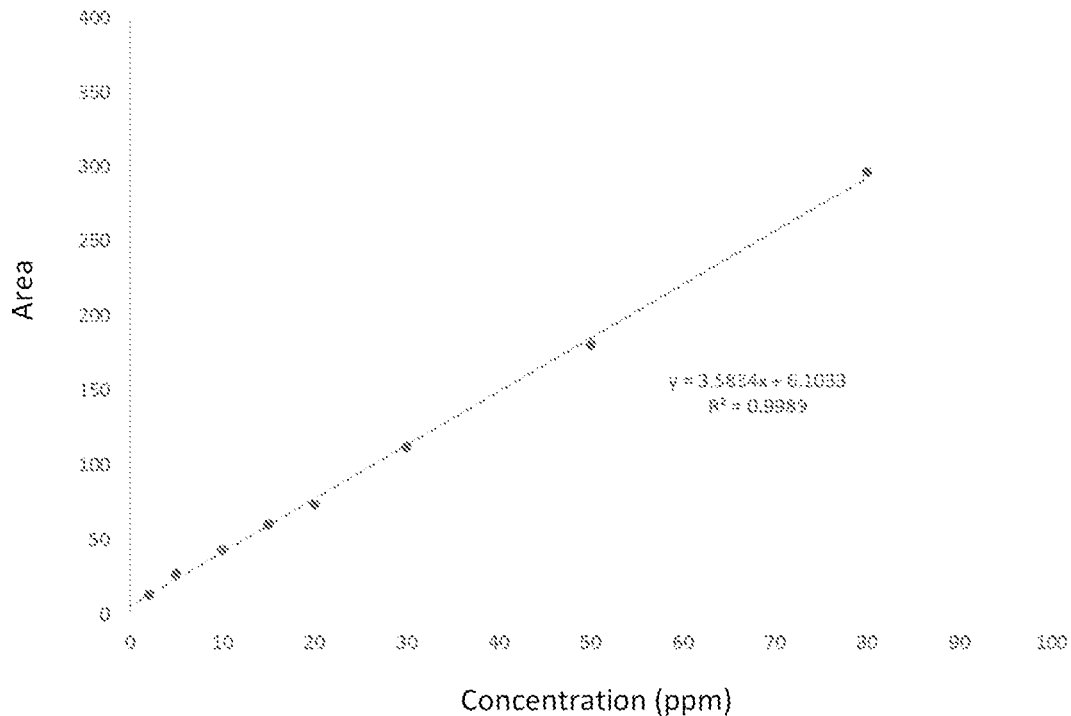
FIG. 12 shows the calibration curve obtained by HPLC of organic ammonium salt 1, OAS-1, in regular gasoline.

Test Procedure:
a) Prepare a standard solution of OAS or SS to be studied at 200 ppm of concentration dissolved in regular gasoline.
b) An aliquot of the standard solution is taken and diluted in regular gasoline to obtain at least five or more solutions in concentrations ranging from 0.5 ppm to 100 ppm.
c) In the HPLC, the detector is programmed at 460 nm, and the samples are injected to obtain their corresponding chromatogram. The chromatogram determines the retention time and the area under the curve corresponding to the signal of the analyzed sample.
d) With the values of area under the curve for the different concentrations, the calibration curve is built, plotting area under the curve vs. concentration,
e) Following the procedure described, the calibration curve shown in FIG. 12 was obtained for the case of organic ammonium salt OAS-1 in regular gasoline.
f) Determination of the concentration of a test sample. To demonstrate that it is feasible to determine the concentration of OAS and/or SS in gasoline through the determination of the area under the curve of chromatograms obtained through the HPLC technique and the use of the generated equations for the case of the OAS-1 product was prepared a sample in Mexican gasoline of the PEMEX-Magna type free of additives with a known concentration, or reference, of 10 ppm, later the area under the curve was determined in the obtained chromatogram, and the concentration of the product in the test samples was calculated through the corresponding equation. The value obtained for the area under the curve was 42.83 milli-absorbance units (mAU), corresponding to a calculated concentration of 10.25 ppm and leading to an absolute error of 2.49% concerning the reference concentration. The result confirms that the HPLC procedure allows us to reliably quantify the concentration of organic ammonium salt (OAS) and/or supramolecular surfactant (SS) in gasoline.

Example 10. Evaluation as a dispersant detergent for the control of deposits through the single-cylinder engine test. The purpose of this method is to evaluate the formation of deposits in the intake valve of a 4 HP single-cylinder internal combustion engine; in this way, it is possible to determine the performance of OAS and SS as gum dispersant detergents for gasoline. Each run has a time of 16 hours, a total of 20 liters of additive-free PEMEX-Magna gasoline is consumed, and the engine speed is adjusted to 2100±100 rpm. The amount of deposits obtained in the intake valve is quantified in milligrams, and the efficiency of the OAS and SS that are evaluated, are determined, taking as reference the deposits that are obtained when using gasoline without additives. It must have a minimum efficiency of 75% to pass this test.

The results of the efficiency of the deposits control obtained for the case of the organic ammonium salts OAS-1 and OAS-4, and the supramolecular surfactants SS-1 and SS-2 of the present invention in the presence of Mexican gasoline of the PEMEX-type Magna free of additives are shown below in Table 3.

TABLE 3

| | | Deposits control | | |
|---|---|---|---|---|
| Supramolecular surfactant | Concentration (ppm) | Deposits on the reference (ppm) | Deposits on the run (mg) | Efficiency (%) |
| OAS-1 | 24 | 3.1 | 1.9 | 38.7 |
| | 18 | 3.1 | 2.1 | 32.2 |
| | 12 | 3.1 | 1.7 | 45.1 |
| | 6 | 3.1 | 1.5 | 51.6 |
| OAS-4 | 24 | 3.1 | 0.4 | 87 |
| | 18 | 3.1 | 0.5 | 83.8 |

TABLE 3-continued

| Supramolecular surfactant | Concentration (ppm) | Deposits control | | |
|---|---|---|---|---|
| | | Deposits on the reference (ppm) | Deposits on the run (mg) | Efficiency (%) |
| | 12 | 3.1 | 0.7 | 77.4 |
| | 6 | 3.1 | 0.9 | 70.9 |
| SS-1 | 24 | 3.1 | 0.6 | 80.6 |
| | 18 | 3.1 | 1.1 | 64.5 |
| | 12 | 3.1 | 1.5 | 51.6 |
| | 6 | 3.1 | 1.9 | 38.7 |
| SS-2 | 24 | 3.1 | 0.4 | 87.1 |
| | 18 | 3.1 | 0.8 | 74.2 |
| | 12 | 3.1 | 1.2 | 61.3 |
| | 6 | 3.1 | 1.7 | 45.2 |

The results in Table 3 show that the organic ammonium salt OAS-4 passes the test for deposits control in a single-cylinder engine from concentrations of 12 ppm, while the supramolecular surfactants SS-1 and SS-2 pass the test from concentrations of 24 ppm.

Likewise, it is observed that OAS-1 does not pass the deposit control test in a single-cylinder engine at the concentrations that its performance was evaluated and that at concentrations of 24 ppm, its deposit removal efficiency was 38.7%. This fact is relevant because SS-1, which passes the single-cylinder engine test at 24 ppm, is derived from OAS-1 and demonstrates the flexibility of our invention to obtain novel products that have traceability and detergent-dispersant properties simultaneously.

It is important to highlight that the organic ammonium salts (OAS) and supramolecular surfactants (SS) of the present invention have several advantages over oxazolidines derived from polyalkyl or poly alkenyl N-hydroxyalkyl succinimides protected in Mexican patent MX269419 and the formulations of hydroxylated polyisobutylene-succinimides and polyethers that are covered in the Mexican patent MX234498. Since the organic ammonium salts (SAO) and the supramolecular surfactants (SS) of the present document simultaneously present traceability and dispersing detergents properties, while the oxazolidines derived from polyalkyl or poly alkenyl N-hydroxyalkyl succinimides of the Mexican patent MX269419 and the formulations of hydroxylated polyisobutylene succinimides and polyethers that are protected in Mexican patent MX234498 only have dispersant detergent properties. In addition to this, the Mexican patent MX269419 shows that to pass the deposit control test in a single-cylinder engine, concentrations of at least 85 ppm of oxazolidines derived from polyalkyl or poly alkenyl N-hydroxyalkyl succinimides are required, while in the present invention, it requires dosages of organic ammonium salts (OAS) or supramolecular surfactants (SS) of at least 12 and 24 ppm, respectively; which represents a great competitive advantage of our organic ammonium salts (OAS) and supramolecular surfactants (SS) object of the present invention concerning the oxazolidines derived from polyalkyl or poly alkenyl N-hydroxyalkyl succinimides of patent MX269419.

Likewise, Mexican patent MX234498 shows that concentrations of at least 165 ppm are required to pass the deposit control test in a single-cylinder engine of the formulations of hydroxylated polyisobutylene succinimides and polyethers, which demonstrates the competitive advantage of our organic ammonium salts (OAS) and supramolecular surfactants (SS) object of the present invention concerning the formulations of hydroxylated polyisobutylene succinimides and polyethers.

The evidence presented shows that it is feasible to apply our organic ammonium salts (OAS) and supramolecular surfactants (SS) as differentiators, markers, tracers, or dyes for fuels that can simultaneously prevent and control the formation of deposits in internal combustion engines.

The invention claimed is:

1. A supramolecular surfactant of structural formula (14):

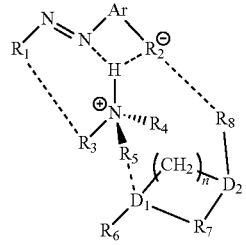

(14)

wherein the surfactant comprises an AZO:A organic ammonium salt of structural formula (13):

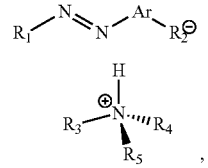

(13)

wherein:

Ar: aromatic, such as an aryl, naphthol, naphthylamide, dimethylaniline, indole, pyrrole, pyrazolone, or substituted quinolones;

$R_1$: is a linear or branched alkyl or alkenyl chain ranging from $C_1$ to $C_{30}$ or a cycloalkyl or aryl group from $C_5$ to $C_{12}$ or aromatics, benzyls, naphthols, naphthylamines, or dimethyl anilines substituted with electron donors selected from $NH_2$, OH, alkyl, and/or electro-attractors selected from the group consisting of COOR (ester), CO (ketone), COOH, CN, $NO_2$, and $SO_3H$;

$R_2$: is a substituent of a protic and/or acidic nature selected from the group COOH, $SO_3H$, and OH;

$R_3$: is H or a linear or branched alkyl or alkenyl chain from $C_1$ to $C_{32}$, or a cycloalkyl or aryl group from $C_5$ to $C_{12}$, or aromatics, benzyls, naphthols, naphthylamines, or substituted dimethyl anilines;

$R_4$: is H, or a linear or branched alkyl or alkenyl chain from $C_1$ to $C_{32}$, or a cycloalkyl or aryl group from $C_5$ to $C_{12}$ or aromatics, benzyls, naphthols, naphthylamines or substituted dimethyl anilines; and $R_5$: a linear or branched alkyl or alkenyl chain from $C_1$ to $C_{32}$, or a cycloalkyl or aryl group from $C_5$ to $C_{12}$, or primary, secondary or tertiary amino alcohols, linear or branched, cyclic or aromatics and/or derived from poly-isobutenyl-succinic anhydrides, poly-isobutylene, poly-isobutenylphenols or Mannich bases, non-covalently interacting with an organic compound OC of structural formula (6),

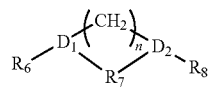
(6)

wherein:
R$_6$: is hydrogen, or a linear or branched alkyl or alkenyl chain ranging from C$_1$ to C$_{32}$, or a cycloalkyl or aryl group from C$_5$ to C$_{12}$, or substituted aromatic and/or derived from poly-isobutenyl-succinic anhydrides, poly-isobutylene, poly-isobutenylphenols or Mannich bases;

R$_7$: is a linear or branched alkyl or alkenyl chain ranging from C$_1$ to C$_{32}$, or a cycloalkyl or aryl group from C$_5$ to C$_{12}$, or substituted aromatic;

R$_8$: is hydrogen, or a linear or branched alkyl or alkenyl chain ranging from C$_1$ to C$_{32}$, or a cycloalkyl or aryl group from C$_5$ to C$_{12}$, or substituted aromatic with —OH and —NH$_2$ groups;

n: it has values between zero and four;

D$_1$: nitrogen with substituents R$_6$ and R$_7$; and

D$_2$: is selected from oxygen, nitrogen, or sulfur as a substituent of the R$_8$ group.

2. The supramolecular surfactant of claim 1, wherein the surfactant comprises the AZO:A organic ammonium salt of structural formula (13) and the OC organic compound of structural formula (6) in a stoichiometric ratio from 4:1 to 1:4.

3. A process for the preparation of a supramolecular surfactant according to claim 1, wherein the process can comprise either Route 1 or Route 2

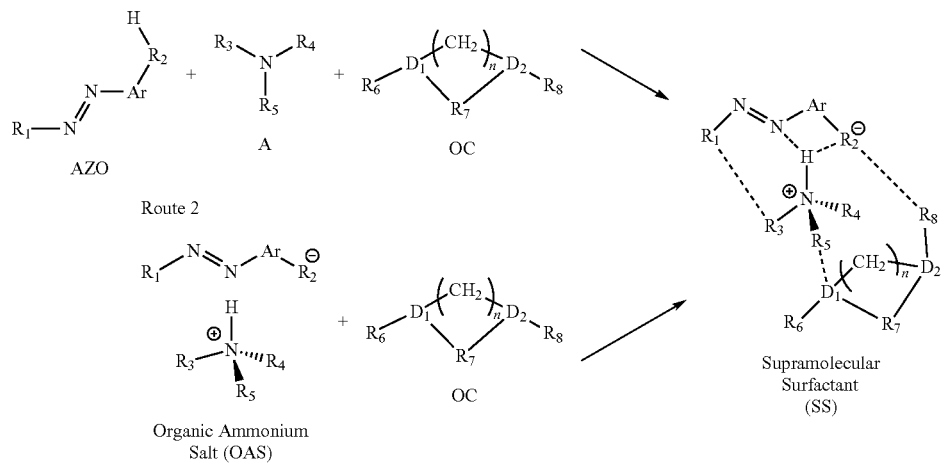

Route 1: mixing an AZO type compound, and an A type compound in a stoichiometric ratio, and adding an organic compound OC in a stoichiometric ratio of 1 to 4 relative to the AZO molecule; then agitating the mixture for 10-240 minutes, at a temperature from 10-120° C.;

Route 2: mixing an AZO:A organic ammonium salt of structural formula (13) with an organic compound OC, in stoichiometric ratio from 4:1 to 1:4; then agitating and homogenizing the mixture mechanically for 10-240 minutes, at a temperature from 10-120° C.

4. The process of claim 3, wherein Route 1 or Route 2 are mass reactions without solvents.

5. The process of claim 3, wherein Route 1 or Route 2 occurs in the presence of an organic solvent, selected from benzene, xylene, xylenes, toluene, light aromatic naphtha, heavy aromatic naphtha, diesel, gasoline, chloroform, and aromatics mixture.

6. The process of claim 5, wherein the solvent proportion relative to the supramolecular surfactant is from 10 to 80% by weight.

7. The supramolecular surfactant of claim 1, wherein the surfactant comprises the AZO:A organic ammonium salt of structural formula (13) and the OC organic compound of structural formula (6) in a stoichiometric ratio from 1.1 to 1:2.

8. The process of claim 3, wherein Route 1 comprises mixing the AZO type compound, and the A type compound in a stoichiometric ratio, and adding the organic compound OC in a stoichiometric ratio of 1 to 2 relative to the AZO molecule; then agitating the mixture for 20-120 minutes, at a temperature from 10-90° C.

9. The process of claim 3, wherein Route 2 comprises mixing the AZO:A organic ammonium salt of structural formula (13) with an organic compound OC, in stoichiometric ratio from 1:1 to 1:2; then agitating and homogenizing the mixture mechanically for 20-120 minutes, at a temperature from 10-90° C.

10. The process of claim 5, wherein the solvent proportion relative to the supramolecular surfactant is from 20-70% by weight.

* * * * *

UNITED STATES PATENT AND TRADEMARK OFFICE
CERTIFICATE OF CORRECTION

Page 1 of 1

PATENT NO. : 12,421,186 B2
APPLICATION NO. : 18/205604
DATED : September 23, 2025
INVENTOR(S) : Ricardo Cerón Camacho et al.

It is certified that error appears in the above-identified patent and that said Letters Patent is hereby corrected as shown below:

In the Claims

Claim 1, Column 26, Line 39, replace "Ar: aromatic, such as an aryl, naphthol," with --Ar: is aromatic selected from aryl, naphthol,--

Claim 1, Column 26, Line 52, replace "selected from the group COOH," with --selected from the group consisting of COOH,--

Claim 1, Column 26, Line 62, replace "$R_5$: a linear or branched alkyl" with --$R_5$: is a linear or branched alkyl--

Signed and Sealed this
Twenty-eighth Day of October, 2025

John A. Squires
*Director of the United States Patent and Trademark Office*